United States Patent
Souza

(10) Patent No.: US 12,049,612 B2
(45) Date of Patent: Jul. 30, 2024

(54) CULTURE PLATES FOR IMAGING

(71) Applicant: Greiner Bio-One North America, Inc., Monroe, NC (US)

(72) Inventor: Glauco Souza, Monroe, NC (US)

(73) Assignee: GREINER BIO-ONE NORTH AMERICA, INC., Monroe, NC (US)

( * ) Notice: Subject to any disclaimer, the term of this patent is extended or adjusted under 35 U.S.C. 154(b) by 835 days.

(21) Appl. No.: 16/630,734

(22) PCT Filed: Jul. 13, 2018

(86) PCT No.: PCT/US2018/041995
§ 371 (c)(1),
(2) Date: Jan. 13, 2020

(87) PCT Pub. No.: WO2019/014541
PCT Pub. Date: Jan. 17, 2019

(65) Prior Publication Data
US 2021/0079329 A1    Mar. 18, 2021

Related U.S. Application Data

(60) Provisional application No. 62/532,031, filed on Jul. 13, 2017.

(51) Int. Cl.
  C12M 1/32    (2006.01)
  C12M 1/00    (2006.01)
  C12M 3/00    (2006.01)

(52) U.S. Cl.
  CPC ............ *C12M 23/12* (2013.01); *C12M 23/22* (2013.01); *C12M 23/38* (2013.01); *C12M 23/46* (2013.01)

(58) Field of Classification Search
  CPC ...... C12M 23/12; C12M 23/22; C12M 23/38; C12M 23/46; C12M 27/16; C12M 33/22
  (Continued)

(56) References Cited

U.S. PATENT DOCUMENTS 5,002,582 A    3/1991 Guire et al.
5,141,718 A *  8/1992 Clark ..................... C12M 23/12
                                              435/297.5

(Continued)

FOREIGN PATENT DOCUMENTS

CN         104480010      4/2015
DE     20 2004 009 793    8/2004
(Continued)

OTHER PUBLICATIONS

Diversified Biotech. WPST-1000. Well Plate Stand. https://web.archive.org/web/20150512182511/https://www.amazon.com/Diversified-Biotech-WPST-1000-Plate-Stand/dp/B00BR3GXWS published May 12, 2015.*

(Continued)

*Primary Examiner* — Benjamin R Whatley
*Assistant Examiner* — Jacqueline Brazin
(74) *Attorney, Agent, or Firm* — Boulware & Valoir PLLC

(57) ABSTRACT

Specialized culture plates for imaging cells in a quick, high throughput manner are provided. Ideally the wells of the culture plate have triangular, square, or V-shaped wells or cell sorting walls having a plurality of vertices, and more complicated variations thereof are also possible. The plates are tilted or rotated to collect the cells at the vertex or vertices of the wells, optionally vibrated to speed the collection, then the vibration and tilt or rotation removed for some period of time, whereon the cells are imaged through the flat transparent bottom of the plate.

13 Claims, 26 Drawing Sheets

(58) Field of Classification Search
USPC ........................................................... 435/29
See application file for complete search history.

(56) References Cited

U.S. PATENT DOCUMENTS

| | | |
|---|---|---|
| 5,225,164 A | 7/1993 | Astle |
| 5,457,527 A | 10/1995 | Manns et al. |
| 6,130,745 A | 10/2000 | Manian et al. |
| 6,340,589 B1 | 1/2002 | Turner et al. |
| 6,503,456 B1 | 1/2003 | Knebel |
| 7,265,829 B2 | 9/2007 | Jiang et al. |
| 7,599,055 B2 | 10/2009 | Gollier et al. |
| 8,512,652 B2 | 8/2013 | Knebel |
| 8,636,965 B2 | 1/2014 | Lohn |
| 8,815,231 B2 | 8/2014 | Souza et al. |
| 8,883,471 B2 | 11/2014 | Souza |
| 9,168,532 B2 | 10/2015 | Malinoski et al. |
| 2001/0030906 A1* | 10/2001 | Friedman ............... C12M 27/16 366/127 |
| 2005/0170498 A1 | 8/2005 | Dolley et al. |
| 2007/0048756 A1* | 3/2007 | Mei ...................... C12Q 1/6883 702/20 |
| 2009/0269799 A1* | 10/2009 | Winkelman .......... G06T 7/0012 435/29 |
| 2010/0216228 A1 | 8/2010 | Love et al. |
| 2010/0248995 A1* | 9/2010 | Kensy .................... B01F 31/22 506/39 |
| 2011/0117634 A1* | 5/2011 | Halamish ............... C12M 23/16 435/283.1 |
| 2011/0286102 A1 | 11/2011 | Jeffs |
| 2013/0037059 A1 | 2/2013 | Stafford |
| 2014/0220672 A1 | 8/2014 | Souza |
| 2014/0322784 A1 | 10/2014 | Souza et al. |
| 2015/0091233 A1 | 4/2015 | Souza et al. |
| 2015/0104844 A1 | 4/2015 | Souza |
| 2016/0032229 A1 | 2/2016 | Egeler et al. |
| 2016/0115437 A1 | 4/2016 | Kim et al. |
| 2016/0272932 A1 | 9/2016 | Precht |
| 2016/0304821 A1* | 10/2016 | Ito ....................... G01N 35/1065 |

FOREIGN PATENT DOCUMENTS

| | | | |
|---|---|---|---|
| DE | 202004009793 | * | 8/2004 |
| DE | 10 2008 008 256 | | 4/2009 |
| DE | 10 2013 113 144 | | 5/2015 |
| EP | 0 483 620 | | 5/1992 |
| EP | 1 007 623 | | 10/2005 |
| EP | 2 338 597 | | 6/2011 |
| JP | 2000513819 B2 | | 10/2000 |
| JP | 2011501689 A | | 1/2011 |
| JP | 4951144 | | 6/2012 |
| JP | 2013504041 A | | 2/2013 |
| JP | 2014521347 A5 | | 10/2014 |
| WO | 2013/019212 | | 2/2013 |
| WO | 2016/069892 | | 5/2016 |

OTHER PUBLICATIONS

Office Action Received in Japanese Application No. JP2020501460 (Feb. 8, 2022) (English Translation submitted).
Castro-Chavez, F., et al., "Effect of lyso-phosphatidylcholine and Schnurri-3 on osteogenic transdifferentiation of vascular smooth muscle cells to calcifying vascular cells in 3D culture," Biochimica et Biophysica Acta, vol. 1830, Issue 6, pp. 3828-3834 (Jun. 2013).
Desai, K.P., et al. "Assembly of Hepatocyte Spheroids Using Magnetic 3D Cell Culture for CYP450 Inhibition/Induction," International Journal of Molecular Science, vol. 18, Issue 5, in Press, pp. 12 (2017).
Ferreira, N.J., et al., "Three-dimensional Bioprinting Nanotechnologies Towards Clinical Application of Stem Cells and their Secretome in Salivary Gland Regeneration," Stem Cells International, Article ID 7564689, vol. 2016, 9 pages.
Haisler, L.W., et al., "Three-dimensional cell culturing by magnetic levitation," Nature Protocols, vol. 8, Issue 10, pp. 1940-1949 (2013).
Souza, R.G., et al., "Magnetically bioprinted human myometrial 3D cell rings as a model for uterine contractility," International Journal of Molecular Sciences, in Press, vol. 18, Issue 4, pp. 10 (2017).
Souza, R.G., et al.,"Three-dimensional tissue culture based on magnetic cell levitation,"Nature Nanotechnology, vol. 5, Issue 4, pp. 291-296 (Apr. 2010).
Timm, M.D., et al., "A high-throughput three dimensional cell migration assay for toxicity screening with mobile device-based macroscopic image analysis," Science Reports, 3:3000, pp. 8 (2013).
Tseng, H., et al., "A high-throughput in vitro ring assay for vasoactivity using magnetic 3D bioprinting," Science Reports, Article No. 6: 30640, pp. 8 (Aug. 1, 2016).
Tseng, H., et al., "A spheroid toxicity assay using magnetic 3D bioprinting and real-time mobile device-based imaging," Science Reports, Article No. 5: 13987, pp. 11 (Sep. 14, 2015).
Tseng, H., et al., "Assembly of a three-dimensional multitype bronchiole coculture model using magnetic levitation," Tissue Engineering, Part C, vol. 19, Issue 9, pp. 665-675 (2013).
Tseng, H., et al., "A three-dimensional co culture model of the aortic valve using magnetic levitation," Acta Biomaterialia, pp. 10 (2014).
International Search Report in International Application No. PCT/US2018/041995, mailed on Feb. 8, 2019.

* cited by examiner

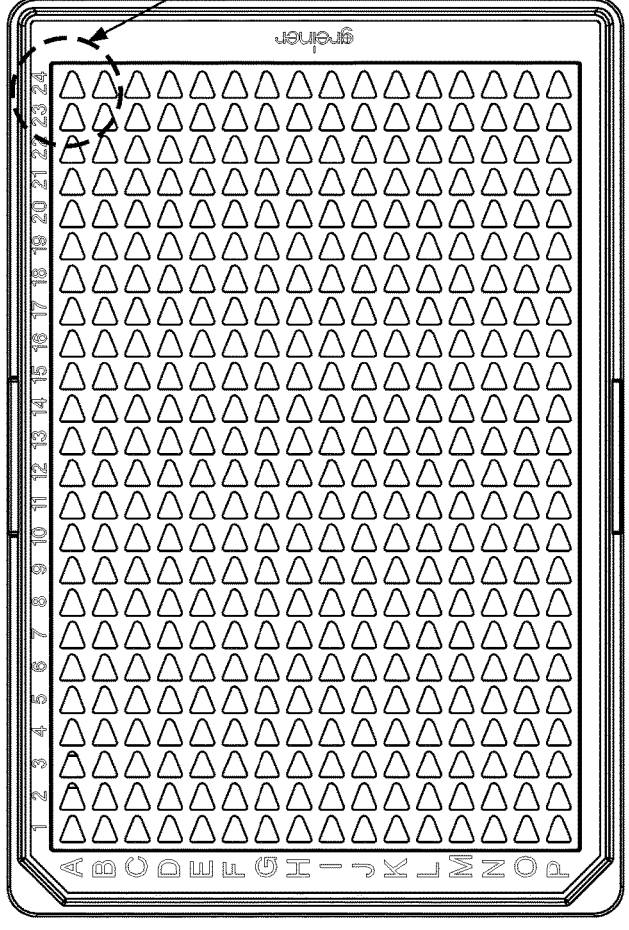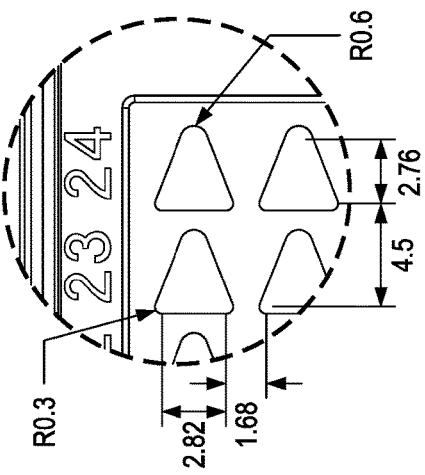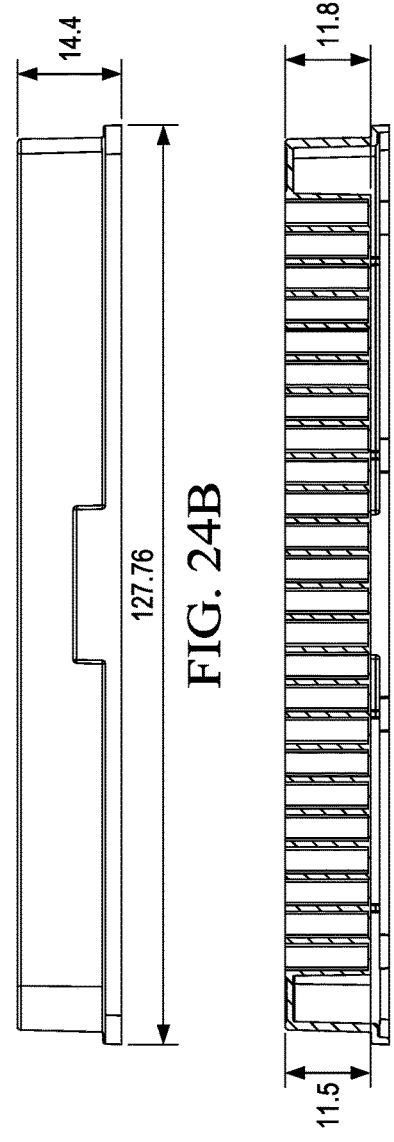
FIG. 24A
FIG. 24B
FIG. 24C
FIG. 24D
FIG. 24E

CULTURE PLATES FOR IMAGING

PRIOR RELATED APPLICATIONS

This application is a National Phase filing under 35 U.S.C. § 371 of International Application PCT/US2018/041995, filed on Jul. 13, 2018, which claims priority to U.S. Ser. No. 62/532,031, filed Jul. 13, 2017. Both applications are incorporated by reference in their entirety for all purposes.

FIELD OF THE DISCLOSURE

The invention relates to various devices and methods for growing, manipulating and imaging cells, which is important in biological research and applications. More particularly, the invention relates to simple, durable and inexpensive vessels for culturing and imaging cells, and methods of making or using same.

BACKGROUND OF THE DISCLOSURE

Cell culturing, which is the growth of cells in an artificial in vitro environment, is a crucial technique in life science research and development. An ideal cell culturing environment is one that promotes fast and robust growth of healthy cells, wherein the cell morphology and function are dominated by cell-cell interactions with other cells, cell-specific signaling, and/or experimental control variables, rather than being influenced by the properties of the artificial culturing environment.

Often, it is desirable to grow cells that closely resemble cells grown in living organisms, including their gene expression, functional characteristics of differentiated cells, morphology, distribution and organization, and the formation of an extracellular matrix. Cost and scalability of production are also critical considerations for the application potential of such technologies.

As such, 3D culturing techniques offer the potential to study cells in a more natural environment, the three-dimensional structure of a group of cells offering the potential to closely mimic the in vivo environment. We have developed a number of materials for allowing 3D culturing of cells in magnetic fields, as well as hardware for manipulating those cells. This application continues the development of hardware, in this case hardware for high throughput imaging of 3D cultures.

SUMMARY OF THE DISCLOSURE

The present invention relates to devices for culturing and imaging cells and 3D cell cultures in high throughout manner. Generally speaking, the invention comprises microtitre plates with a plurality of wells, the wells having a triangular or other shape having at least one vertex in cross section in top plan view, but with a flat, optically clear base.

U.S. Pat. No. 5,225,164 describes square wells having a flat base, but the interior of those wells comprises a baffle, designed to allow mixing of fluids in. Further, those plates are not transparent. Thus, those plates cannot be used for imaging.

Cultures can be grown in the plates of the invention, the same as in any other microtitre plate. They can also be grown in 3D culture with the use of magnet fields and cell magnetizing materials, such as NanoShuttle®. Alternatively, cells can be grown in 3D in suspension or in gel/scaffold type materials by other methods, or added to the plates after growth.

The plates are tilted manually or with a dedicated stand or machine, such that the cells fall to the vertex of well. When the plate is again slowly and carefully leveled, the 3D culture will remain at that vertex, settling to the bottom of the plate with gravity or with a magnetic field, and the 3D cell culture can then be imaged through the bottom of the plate. The cells will thus be at a known location at the bottom corner of the plate and the plate will be positioned flat relative to the imaging machine, allowing faster throughput and improved imaging of the plate through an imaging machine. Importantly, all of the cells will be at the same depth of field, allowing a single image to capture multiple wells and even multiple plates.

Particularly preferred is a transparent plate with clear flat bottoms for best imaging, and preferably in standard microtitre plate sizing. The plate can be made in one or more parts, depending on whether temperature cycling is expected and the quality of imaging that is needed. If desired, the bottom of the plate can be a clear, transparent optical glass for best imaging, but for many purposes, the typical thin-well polypropylene, polypropylene, polyolefin, glass-filled polypropylene, acrylbutadienestyrene (ABS), polyamide (PA), polycarbonate (PC), polystyrene (PS), polymethyl methacrylate (PMMA), polypropylene (PP) or styrene acrylonitrile (SAN), and the like will suffice. Examples of suitable transparent polymers are clear polystyrene, polyacrylonitrile, polycarbonate, polyester, polymethyl pentene and acrylic materials, but there are many variations of transparent polymers.

The cell culture plates can be manufactured by any method known in the art, see e.g., U.S. Pat. Nos. 5,002,582, 5,457,527, 6,503,456, 6,340,589, US20050170498, U.S. Pat. Nos. 8,512,652, 8,636,965, 9,168,532, and the like.

The compatibility of plates with automated equipment is perhaps one of the most stringent constraints on the form and structure of plates that are to be used in high throughput methods. Many laboratories automate various steps or phases of procedures, such as depositing and removing small quantities of reaction mixture from sample wells using automated dispensing/aspiration systems. Furthermore, plate-handling equipment is often used to help facilitate the automation of such procedures. Accordingly, it is desirable to use a multiwell plate that is conducive to use with robotic equipment and can withstand robotic gripping and manipulation. Standard dimensions have been recommended by the SLAS Microplate Standards Advisory Committee at slas.org/resources/information/industry-standards/and are thus a preferred embodiment.

Any imaging system can be used to image the plates, preferably imaging one or more plates at a time. U.S. Pat. Nos. 7,599,055, 7,265,829, US20110286102, U.S. Pat. No. 6,130,745, and the like are exemplary, but we have successfully imaged plates using a smart phone and a simple camera stand per US20150091233. However, for maximal throughput, it is envisioned that a dedicated system will be provided for rapid imagery of several plates simultaneously.

As used herein "vessel" or "plate" refers to any container for culturing cells, such as a Petri dish, flask, microfluidic chips, microfluidic devices, multiwell culturing plate, test tubes, and the like. Although standard microtitre plates are currently preferred, it is expected that the art will migrate to a microfluidic device in the future as such devices become more robust and standardized and handling equipment for same becomes ubiquitous.

As used herein, a "vertex" is an angular point of a polygon, polyhedron, or other figure. For example, a triangle has three vertexes, a v-shaped well has three vertexes, and a square has four. Although at least one vertex is required herein, the remainder of the shape need not be polygonal, as indicated by the teardrop shape in FIG. 10.

As used herein, a "V-shaped" well describes the cross section of a well having two legs meeting at one point or vertex, as does the letter "V". A v-shaped well may be very beneficial in certain applications where the cells can be collected at one leg of the V and the other used to change media, thus minimizing any disruption to the cells. Two different cell types can be culture at different ends of the legs, and then later brought together at the vertex of the two legs, thus allowing assays involving two cell types.

A "rounded vertex" means that the point where the two straight lines of a polygon or partial polygon meet is truncated slightly in a smooth curve. The rounded vertex allows a larger clump of cells to accumulate at the vertex.

By "over said well", we mean that the magnetic lid and the magnets cannot dip into the culture media when the magnet is in use, but sits over, below, or beside the culture media. The device can also sit under the entire plate, in which orientation, the media is not contacted either.

By "microplate" or "microtitre plate" or "microtitre vessel" what is meant are the then current industry standard microplates. Note that ANSI-SLAS publishes standard sizes for microtitre plates in order to ensure interoperability to robotics and multi-pipettors, and these can be found at slas.org/resources/information/industry-standards/.

"Magnet" refers to any material creating a magnetic field and field shape and can be a permanent magnet or an electromagnet.

As used herein, a "magnetic driver" is a lid or cover or bottom that can fit over or under a culture plate and has magnets permanently or reversible affixed thereto, such that magnetic driver can be used with the plate to levitate and/or pattern/print cells being cultured in the plate.

Reference to the "under" surface of a cap is with respect to the lip, the under surface having a lip or edge on the same side.

As used herein, a "culture plate system" refers in general to a system including a culture plate, such as any of those described herein, a cap having a lip around an outer circumference thereof and being shaped to fit over or under said culture plate and a means for tilting or rotating said culture plate. Particularly, the term refers to a system including microtiter plate, a matching lid, a magnetic lid or driver, and a wedge for tilting the plate. Means for tilting can also be a rocker plate or any device specially designed to tilt plates. Means for rotating cells can be any rotating platform.

As used herein, a "sorting wall" is a wall that is lower than exterior walls of a well, such that medium can flow over top of the sorting wall. The walls have a plurality of vertices, allowing cells to collect at each vertex. Such sorting walls are preferably zigzag (alternate facing Vs), as this is the simplest, but any line with a plurality of vertices could be use (e.g., alternate facing open face boxes or open face pentagons).

The invention includes any one or more of the following embodiments, in any combination(s) thereof:

A multiwell culture plate, comprising:
a rectangular plate having a first and second long side and a first and second short side;
said plate having a plurality of wells; and
each of said plurality of wells having a non-circular cross section having at least one vertex when viewed from a top view; and
each of said wells having a flat transparent base lacking any obstruction, such that the entirety of the well contents can be imaged from underneath the base.
A multiwell culture plate, comprising:
a rectangular plate having a first and second long side and a first and second short side;
said plate having a plurality of wells; and
each of said plurality of wells having a V-shaped cross section when viewed from a top view, said V-shaped cross section having a vertex; and
each of said wells having a flat base, in particular a flat transparent base.
A multiwell culture plate, comprising:
a rectangular plate having a first and second long side and a first and second short side;
said plate having a plurality of wells; and
each of said plurality of wells having a triangular cross section when viewed from a top view, said triangular cross section having a vertex; and
each of said wells having a flat base, in particular a flat transparent base.
Any multiwell culture plate herein said cross section shape being a triangle, isosceles triangle, square, rectangular, V-shaped, parallelogram, or teardrop shaped and further having zero, one or more rounded corners (aka vertexes).
Any multiwell culture plate herein, said vertex oriented to said first long side.
Any multiwell culture plate herein, further comprising a rectangular wedge that fits under said rectangular cell culture vessel thus lifting said second long side by 15-45°.
Any multiwell culture plate herein, said vertex oriented to said first short side.
Any multiwell culture plate herein, further comprising a rectangular wedge that fits under said rectangular cell culture vessel thus lifting said second short side by 15-45°.
Any multiwell culture plate herein, said vertex having a rounded corner.
Any multiwell culture plate herein, further comprising a rectangular cap having a lip around an outer circumference thereof and being shaped to fit over or under said multiwell culture plate.
Any multiwell culture plate herein, further comprising a rectangular cap having a lip around an outer circumference thereof and being shaped to fit over or under said multiwell culture plate, said cap having a plurality of magnets affixed thereto, thus holding said magnet over each said well when said cap is in place over or under said multiwell culture plate.
Any multiwell culture plate herein, further comprising a rectangular cap having a lip around an outer circumference thereof and being shaped to fit over or under said multiwell culture plate, said cap having a plurality of magnets affixed thereto, thus holding said magnet over each said well when said cap is in place over or under said multiwell culture plate, each adjacent magnet being in an opposite polarity.

-continued

Any multiwell culture plate herein, wherein each said magnet sits over each said vertex.
Any multiwell culture plate herein, wherein each said magnet sits over a center of each well.
Any multiwell culture plate herein, having 6, 12, 24, 96, 384, 1536, 3072, 6144 wells.
A method of imaging a cell culture, comprising:
incubating one or more cell types in a medium in one or more wells of the multiwell culture plate herein;
tilting said multiwell culture plate so that cells collect at said vertex;
optionally vibrating said plate;
removing said tilt when all cells have collected at said vertex; and
imaging said cells through said flat base, in particular transparent flat base.
A method of imaging a cell culture, comprising:
incubating one or more cell types in a medium in one or more wells of the multiwell culture plate herein;
fitting said wedge under said multiwell culture plate,
optionally vibrating said plate;
removing said wedge when all cells have collected at said vertex; and
imaging said cells through said flat base, in particular transparent flat base.
Any method herein, wherein said vibrating step is performed.
A method of imaging a cell culture, comprising:
a)    incubating one or more cell types in a medium in one or more wells of a multiwell culture plate
wherein each well has a transparent flat base;
b)    tilting said multiwell culture plate;
c)    vibrating said multiwell culture plate;
d)    collecting all cells at a lowest location of said one or more wells of said tilted multiwell culture plate;
e)    ceasing said tilting and said vibrating; and
imaging said cells through said transparent flat base.
Any method herein where said one or more wells have a triangular or a square or a V-shaped cross section
having at least one vertex, and wherein said tilting allows cells to collect at said vertex.
Any method herein, wherein said vertex has a rounded corner.
A multiwell culture plate, comprising:
i)    a rectangular plate having a long side and a short side;
ii)    said plate having a plurality of wells; and
iii)    each of said plurality of wells having a V-shaped cross section at abase of said wells, said V-
shaped cross section having a vertex and a first leg and a second leg;
iv)    wherein said first legs of each well in a single row are connected near a top surface of said plate,
thus forming a channel connecting all wells in said row; and
v)    each base being a flat transparent base.
In a further variation, the channel connecting the rows of V-shaped wells can connect to an end channel
connecting every row. See FIG. 17.
A method of imaging a cell culture, comprising:
a)    incubating one or more cell types in a medium in one or more wells of the v-shaped multiwell
culture plate;
b)    tilting said multiwell culture plate;
c)    vibrating said multiwell culture plate;
d)    collecting all cells said vertex of each well in said tilted multiwell culture plate;
e)    ceasing said tilting and said vibrating; and
f)    imaging said cells through said transparent flat base.
In this method, wherein said tilting to an opposite end of the said vertex, allows cells from a row of wells
to be collect together, which can be beneficial in certain assays.
A culture plate, comprising: i) one or more large well(s) with a wall of height H and a flat transparent base;
ii) said large well(s) each having a plurality of sorting walls having a plurality of vertices, said sorting
walls of height < H. Preferably the sorting walls are zigzag, but other walls having a plurality of vertices
are possible.
Any culture plate herein described, wherein said culture plate has a single rectangular well, and said
plurality of zigzag sorting walls are arranged in parallel to each other and traverse from one side of said
rectangular well to another side of said rectangular well.
Any culture plate herein described, wherein said culture plate has a single circular well, and said plurality
of zigzag sorting walls are arranged in parallel to each other and traverse from one side of said circular
well to another side of said rectangular well.
Any culture plate herein described, wherein said culture plate has a single circular well, and said plurality
of zigzag sorting walls are arranged in concentric circles to each other centered on a center of said circular
well.
Any culture plate herein described, wherein said culture plate has a single circular well, and said plurality
of zigzag sorting walls are arranged radially from a center of said circular well.
A method of imaging a cell culture, comprising:
a)    incubating one or more cell types in a medium in a culture plate having sorting walls with a
plurality of vertices, as described herein;
b)    tilting or rotating said culture plate;
c)    vibrating said culture plate;
d)    collecting cells at said plurality of vertices;
e)    ceasing said tilting or rotating and said vibrating for a period of time; and,
f)    imaging said cells through said transparent flat base.
A multiwell culture plate system, comprising:
a)    a multiwell culture plate as described herein;
b)    a cap having a lip around an outer circumference thereof and being shaped to fit over or under
said culture plate;

-continued c)   a means for tilting said culture plate.
A culture plate system, comprising:
a) a culture plate having sorting walls with a plurality of vertices, as described herein;
b) a cap having a lip around an outer circumference thereof and being shaped to fit over or under said culture plate;
c) a means for tilting said plate, or a means for rotating said plate.

Specific Embodiments

In a specific embodiment, the present invention further pertains to:
A multiwell culture plate system, comprising:
a rectangular plate having a first and second long side and a first and second short side, said plate having a plurality of wells; and each of said plurality of wells having a non-circular cross section having at least one vertex when viewed from a top view, and each of said wells having a flat transparent base lacking any obstruction, such that the entirety of the well contents can be imaged from underneath the base,
a rectangular cap having a lip around an outer circumference thereof and being shaped to fit over or under said plate,
a means for tilting said plate.
A multiwell culture plate system, comprising:
a rectangular plate having a first and second long side and a first and second short side, said plate having a plurality of wells; and each of said plurality of wells having a V-shaped cross section when viewed from a top view, said V-shaped cross section having a vertex, and each of said wells having a flat base, in particular a flat transparent base.
a rectangular cap having a lip around an outer circumference thereof and being shaped to fit over or under said plate,
a means for tilting said plate.
A multiwell culture plate system, comprising:
a rectangular plate having a first and second long side and a first and second short side, said plate having a plurality of wells; and each of said plurality of wells having a triangular cross section when viewed from a top view, said triangular cross section having a vertex, and each of said wells having a flat transparent base.
a rectangular cap having a lip around an outer circumference thereof and being shaped to fit over or under said plate,
a means for tilting said plate.
Any multiwell culture plate system herein said cross section shape being a triangle, isosceles triangle, square, rectangular, V-shaped, parallelogram, or teardrop shaped and further having zero, one or more rounded corners (aka vertexes).
Any multiwell culture plate system herein, said vertex oriented to said first long side.
Any multiwell culture plate system herein, said vertex oriented to said first short side.
Any multiwell culture plate system herein, wherein said means for tilting the rectangular multiwell culture plate is a rectangular wedge that fits under said rectangular multiwell culture plate thus lifting a short side or a long side of the rectangular multiwell culture plate by 15-45°.
Any multiwell culture plate system herein, said vertex having a rounded corner.

Any multiwell culture plate systems herein, further comprising a rectangular cap having a lip around an outer circumference thereof and being shaped to fit over or under said rectangular multiwell culture plate, said cap having a plurality of magnets affixed thereto, thus holding said magnet over each said well when said cap is in place over or under said multiwell culture plate, each adjacent magnet being in an opposite polarity.
Any multiwell culture plate system herein, wherein each said magnet sits over each said vertex.
Any multiwell culture plate system herein, wherein each said magnet sits over a center of each well.
Any multiwell culture plate system herein, having 6, 12, 24, 96, 384, 1536, 3072 or 6144 wells.
A method of imaging a cell culture, comprising:
a) incubating one or more cell types in a medium in one or more wells of the plate of the multiwell plate system herein;
b) tilting said plate so that cells collect at said vertex;
c) optionally vibrating said plate;
d) removing said tilt when all cells have collected at said vertex; and
e) imaging said cells through said flat base, in particular said flat transparent base.
A method of imaging a cell culture, comprising:
a) incubating one or more cell types in a medium in one or more wells of the plate of the multiwell plate system herein;
b) fitting a wedge under said plate,
c) optionally vibrating said plate;
d) removing said wedge when all cells have collected at said vertex; and
e) imaging said cells through said flat base, in particular said flat transparent base.
Any method herein, wherein said vibrating step is performed.
A method of imaging a cell culture, comprising:
a) incubating one or more cell types in a medium in one or more wells of a plate of the multiwell plate system herein, wherein each well has a flat transparent base;
b) tilting said plate of the multiwell plate system;
c) vibrating said plate of the multiwell plate system;
d) collecting all cells at a lowest location of said one or more wells of said tilted plate of the multiwell plate system;
e) ceasing said tilting and said vibrating; and
f) imaging said cells through said flat transparent base.
Any method herein where said one or more wells have a triangular or a square or a V-shaped cross section having at least one vertex, and wherein said tilting allows cells to collect at said vertex.
Any method herein, wherein said vertex has a rounded corner.
A multiwell culture plate system, comprising:
a rectangular plate having a long side and a short side, said plate having a plurality of wells; and each of said plurality of wells having a V-shaped cross section at a base of said wells, said V-shaped cross section having a vertex and a first and a second leg; wherein said first legs of each well in a single row are connected near a top surface of said plate, thus forming a channel connecting all wells in said row; and each base being a flat transparent base, a rectangular cap having a lip around an outer circumference thereof and being shaped to fit over or under said plate, a means for tilting said plate.

In a further variation, the channel connecting the rows of V-shaped wells can connect to an end channel connecting every row.

A method of imaging a cell culture, comprising:
a) incubating one or more cell types in a medium in one or more wells of the v-shaped plate of the multiwell culture plate system herein;
b) tilting the plate of the multiwell culture plate system;
c) vibrating said plate of the multiwell culture plate system;
d) collecting all cells at said vertex of each well in said tilted plate of the multiwell culture plate system;
e) ceasing said tilting and said vibrating; and
f) imaging said cells through said flat transparent base.

In this method, wherein said tilting to an opposite end of the said vertex, allows cells from a row of wells to be collect together, which can be beneficial in certain assays.

BRIEF DESCRIPTION OF THE DRAWINGS

FIG. 20A shows the plate empty, and FIG. 20B shows the plates with each vertex of a zigzag sorting wall having collected some cells due to the rocking motion washing the medium back and forth over the shorter sorting walls. The cell sorting walls are about half the height of the exterior walls, and can be anywhere from 0.5-50% of the exterior walls, the greater height needed to retain any sloshing medium. In FIG. 20C the rocking has ceased, and the cells have grown into clumps.

FIG. 24A-E Top (A), side (B, C), cross sectional (D) and enlarged (E) views of a 384-well plate, each well of the 384-well plate having a triangular cross section.

DETAILED DESCRIPTION

Figure 1A:
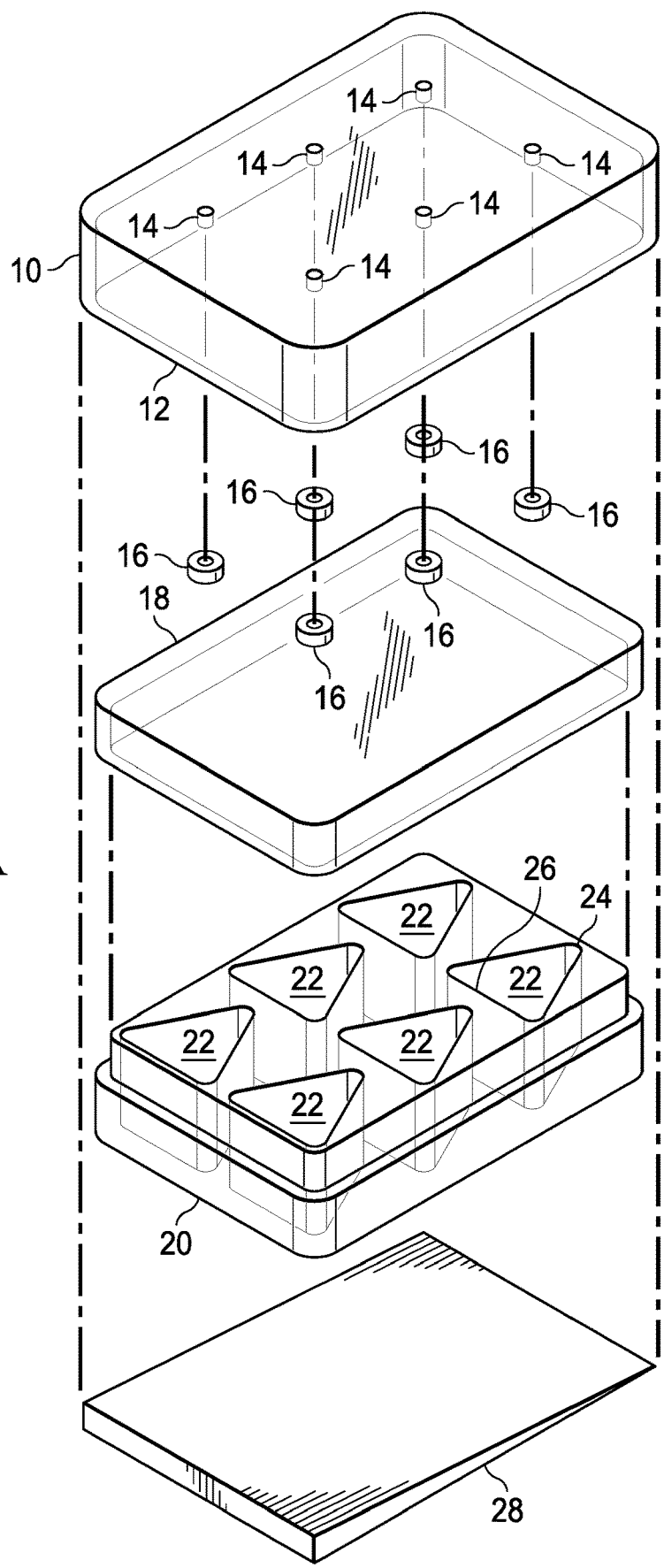
FIG. 1A. Perspective view of six-well plate with magnetic lid, regular lid, and wedge. Each well has a triangular cross section in top view.

In FIG. 1A, we see one embodiment of a multiwell culture plate system, including microtitre plate, matching lid, a magnetic lid or driver, and wedge for tilting the plate. Magnetic lid 10 can be used over or under the plate when used in magnetic culturing, as described in inventors' prior patents. Second lid 18 is a typical lid, and is provided for use over the cells when the magnetic lid 10 is used under the cells. Magnetic lid 10 has an edge or rim 12 circumnavigating the lid and sized to fit over or under the plate. The inner surface of the lid in this case has pillars 14 each arranged to center over a corresponding well when in place over or under the plate. Ring magnets 16 are fitted over the pillars 14, and preferably each magnet is oriented to be in opposite polarity to its nearest neighbors. However, the pillars are only one way of attaching magnets, and any other method could be used including depressions into which the magnets fit, or the magnets could be glued to the lid.

A second lid 18 is also shown, also having an edge or rim circumnavigating the lid and sized to fit over the plate.

Base 20 has 6 triangular wells 22, having vertex 24 opposite flat side 26. In this case, the flat side 26 is oriented against one of the long sides of the rectangular plate, the vertex 24 pointing to the opposite long edge, but other orientations are possible, the wedge adapted accordingly. Wedge 28 is sized to have similar dimensions to the plate, but is thicker on one side, this providing a 15-45°, preferably about 30-35°, of lift when slipped under the base, directing the cells to settle at one vertex of the triangular well. This results in a change in gravity orientation, which results in cells settling along the vertex 24 of the triangular well, such that when again placed horizontally, the cells will settle on the base at that vertex.

Figure 1B:
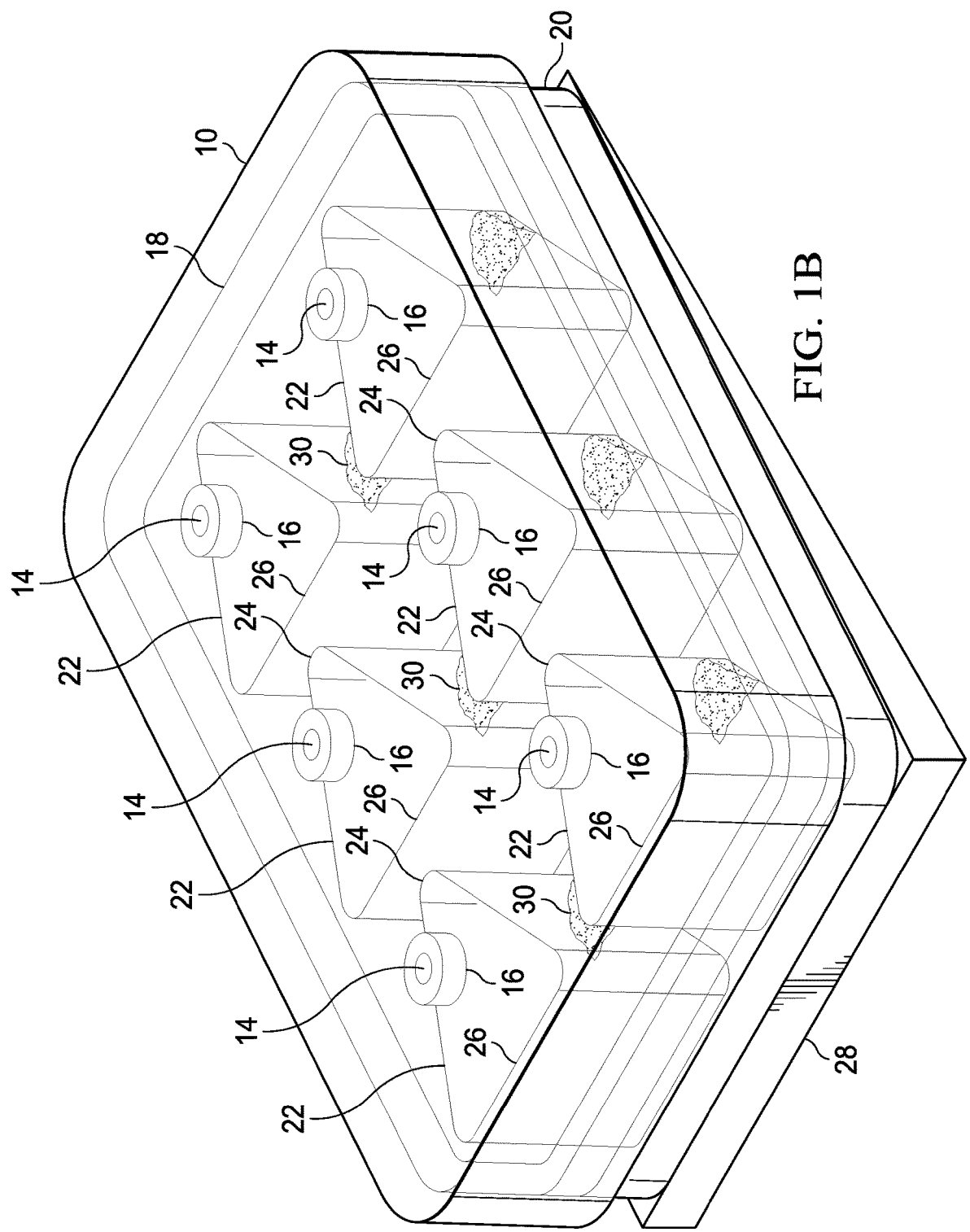
FIG. 1B. Assembled six-well plate with wedge in place thereunder, thus tilting plate.
Figure 1C:
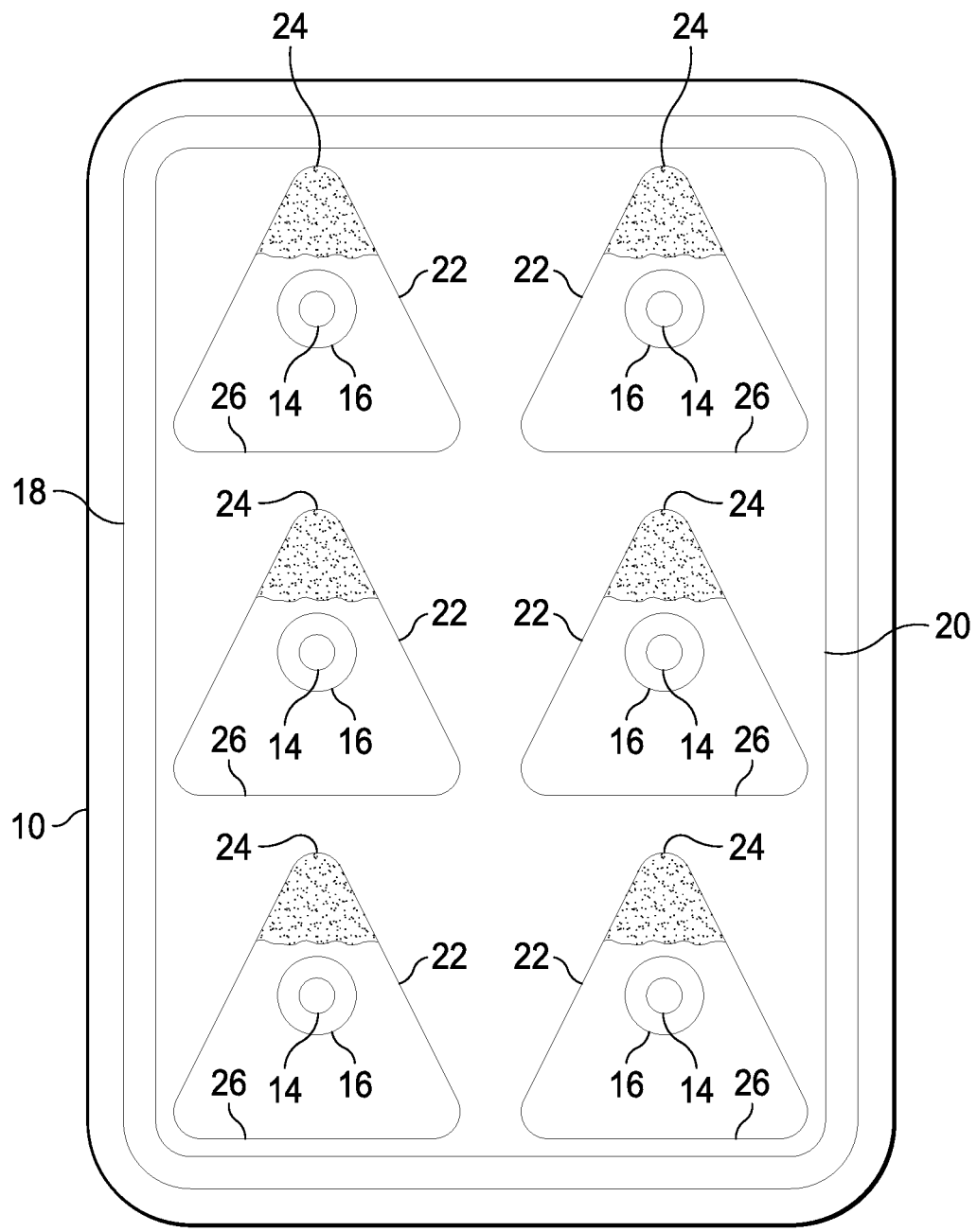
FIG. 1C. Top view of six-well plate with cells collected at vertex of triangle for convenient viewing.

FIG. 1B is a perspective view with wedge 28 under base 20, lifting it up on the flat side, with cells 30 settling into vertex 24. FIG. 1C is a top view of base 20, clearly showing cells 30 settling at vertex 24. When the plate is carefully set on an imager, e.g., a camera, the cells can be photographed through the bottom of the plate, and all will be collected at the same vertex and at about the same depth. This makes imaging faster and provides higher quality, all the cells being at about the same depth and same approximate location.

FIG. 1 showed a 6 well plate, but the same principles can be used for 12-, 24-, 48-, 96- 384-, and 1,536-, 3,072-, 6,144-well formats, and so on.

Figure 2:
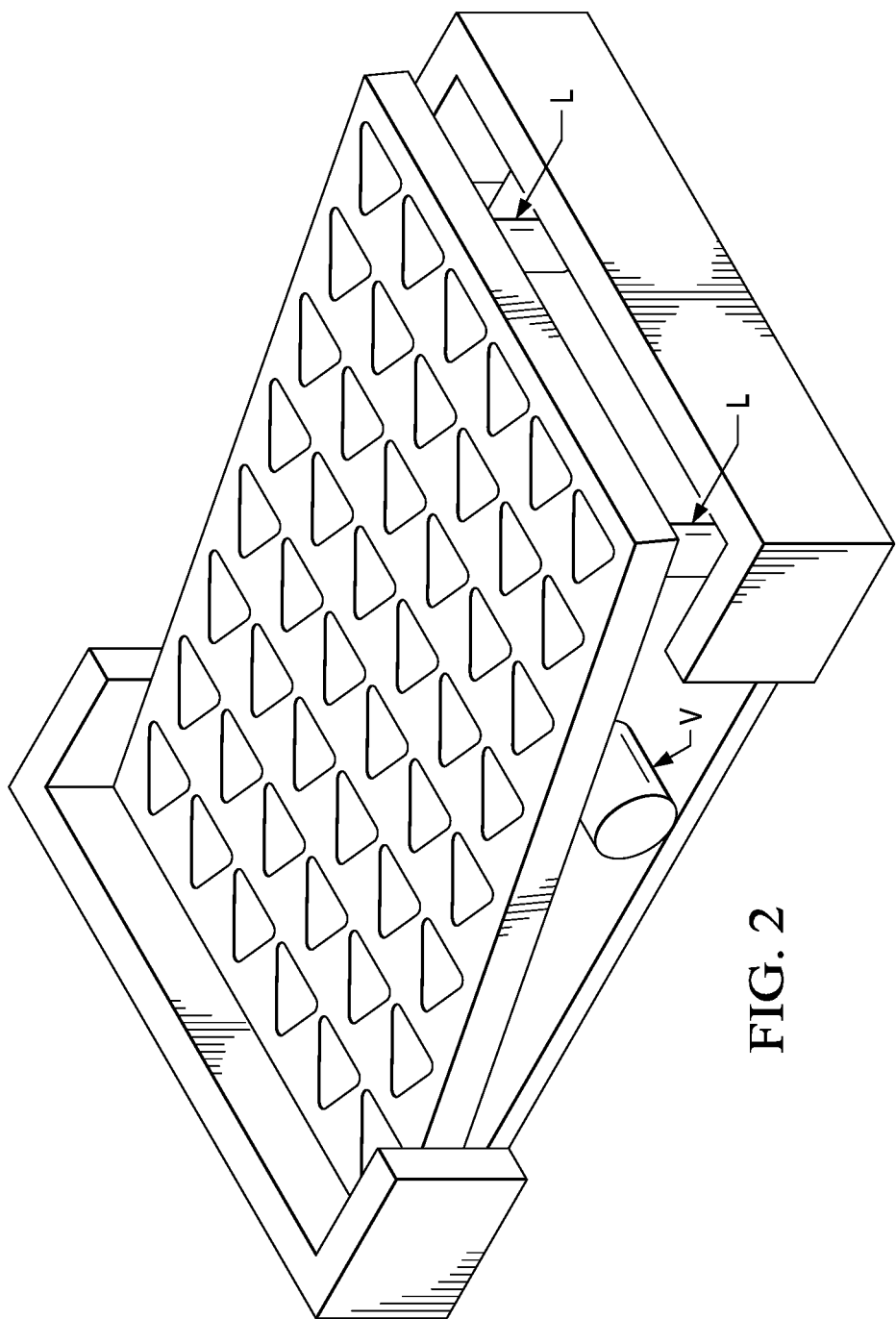
FIG. 2. Perspective view of a prototype single plate stand with lift mechanism, vibrating mechanism and frame to support plate in lifted position. Vibrator (V) and lift mechanism (L) indicated by letter label.
Figure 4:
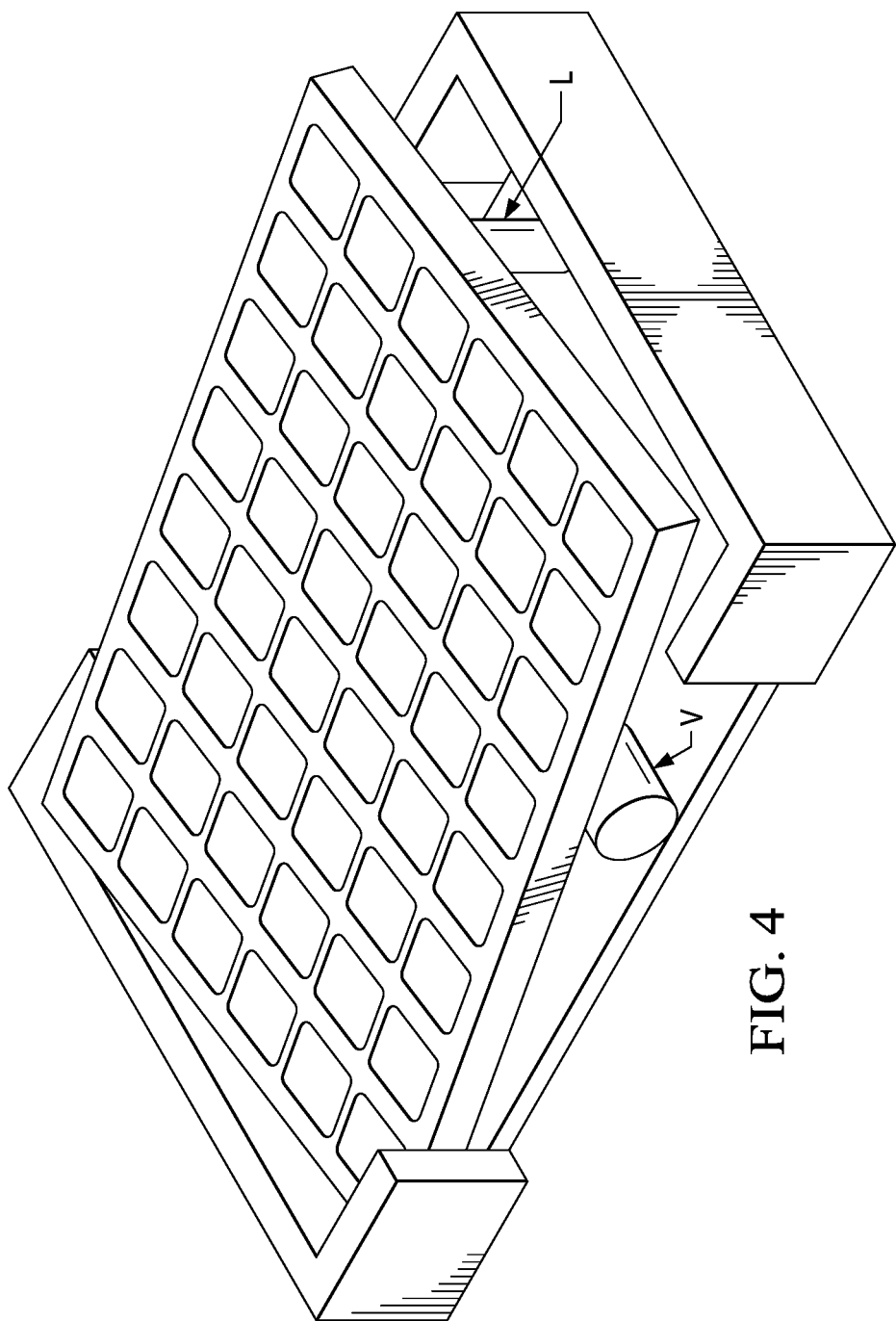
FIG. 4. Another embodiment of a prototype stand wherein the plates are tilted in both axes. Vibrator (V) and lift mechanism (L) indicated by letter label.
Figure 6:
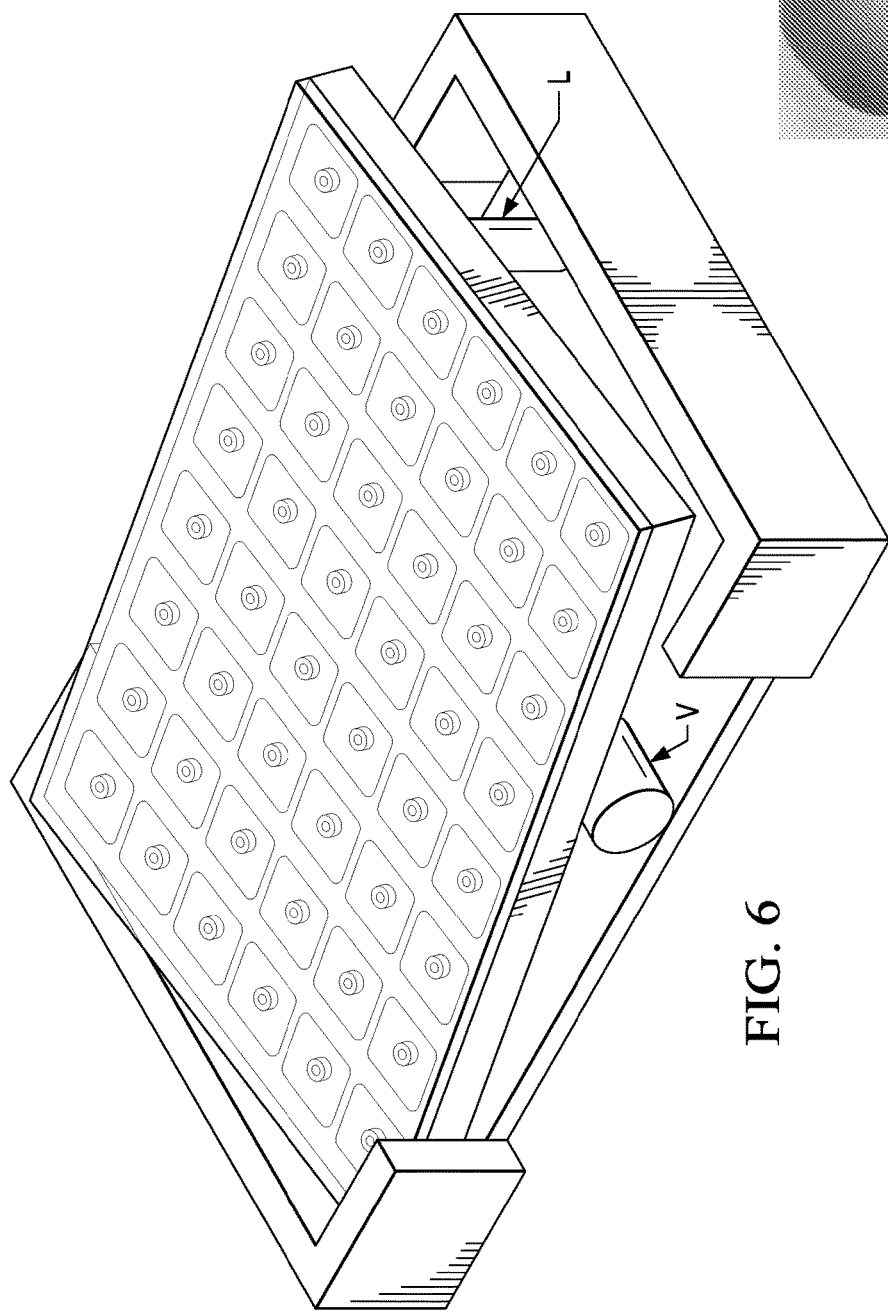
FIG. 6. Stand together with magnetic lid with magnets placed under the vertex and microtitre plate. Vibrator (V) and lift mechanism (L) indicated by letter label.
Figure 8:
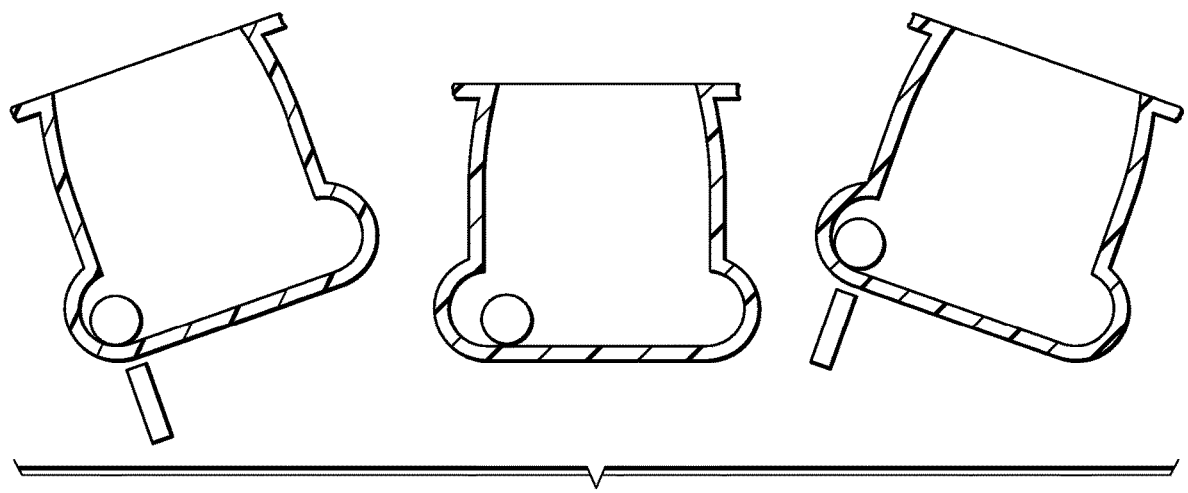
FIG. 8. Example of inclined stand and magnet (small rectangle) used in cell and media manipulations.
Figure 10:
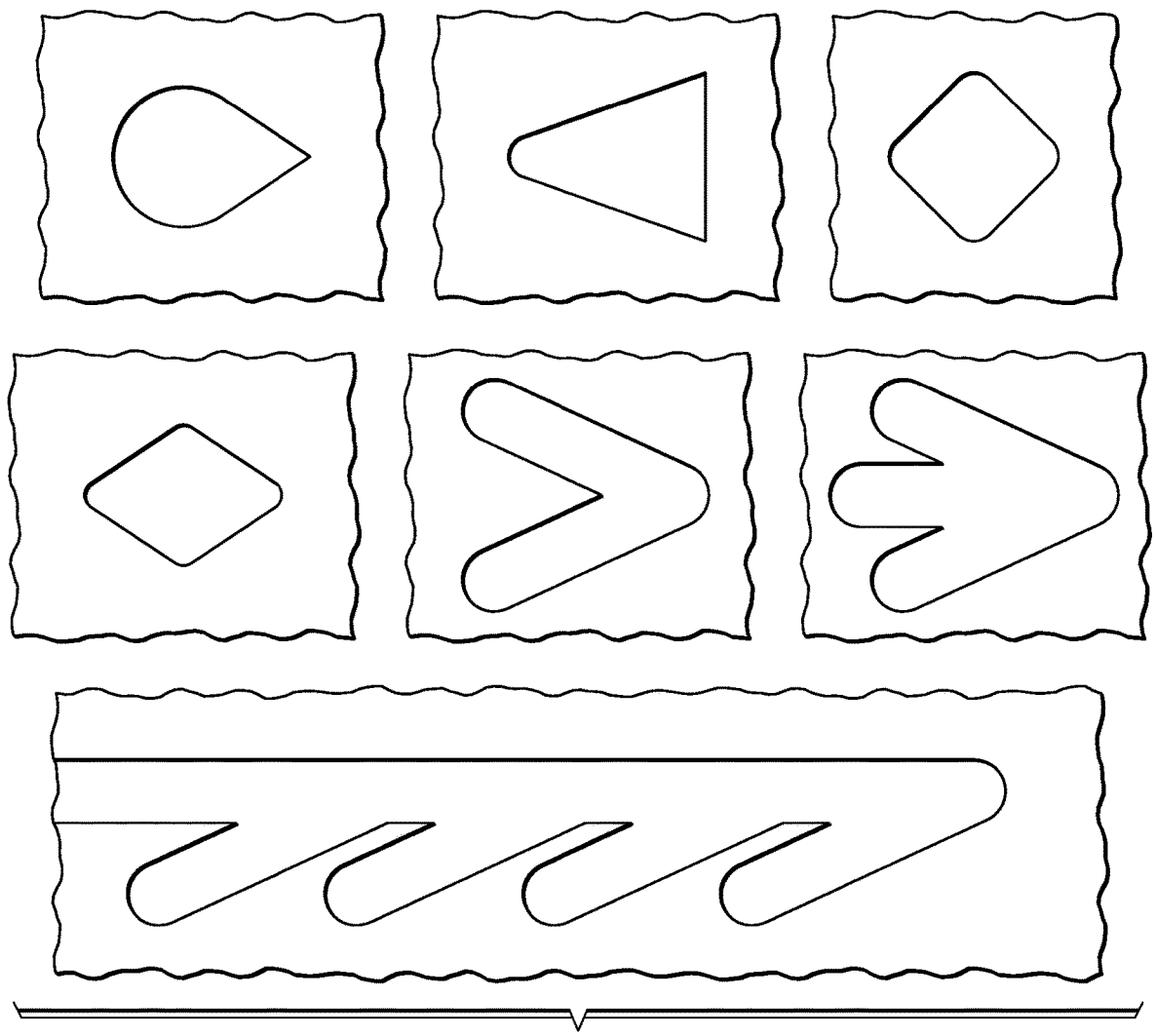
FIG. 10. Various well shapes (top view).
Figure 11:
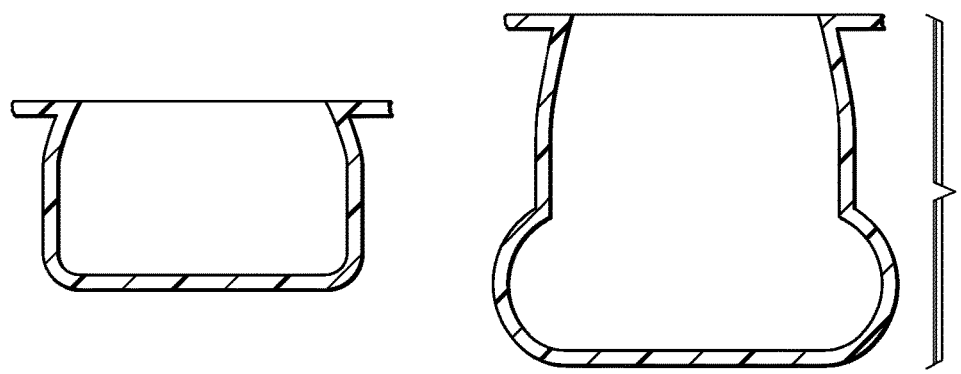
FIG. 11. Various well shapes (side view).
Figure 17:
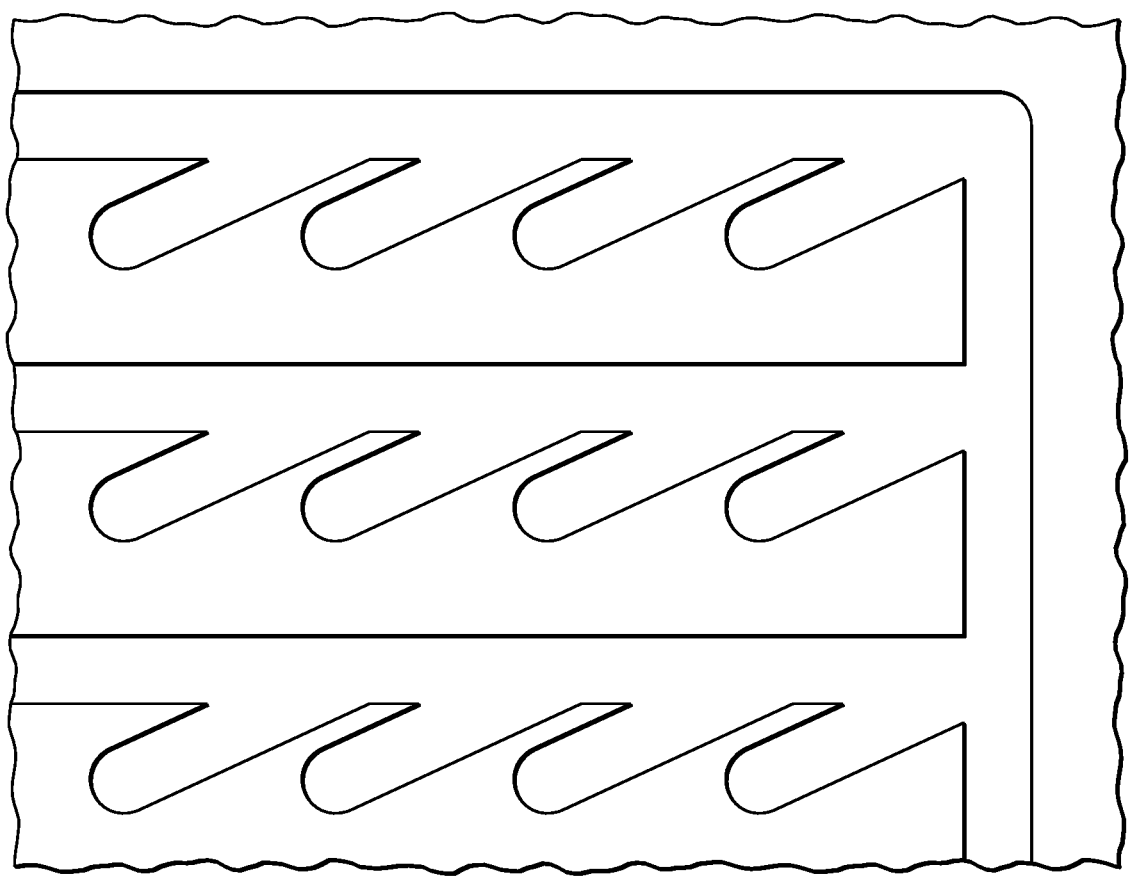
FIG. 17. Another embodiment of a multichannel well, wherein all of the channels combined into an end channel.
Figure 18:
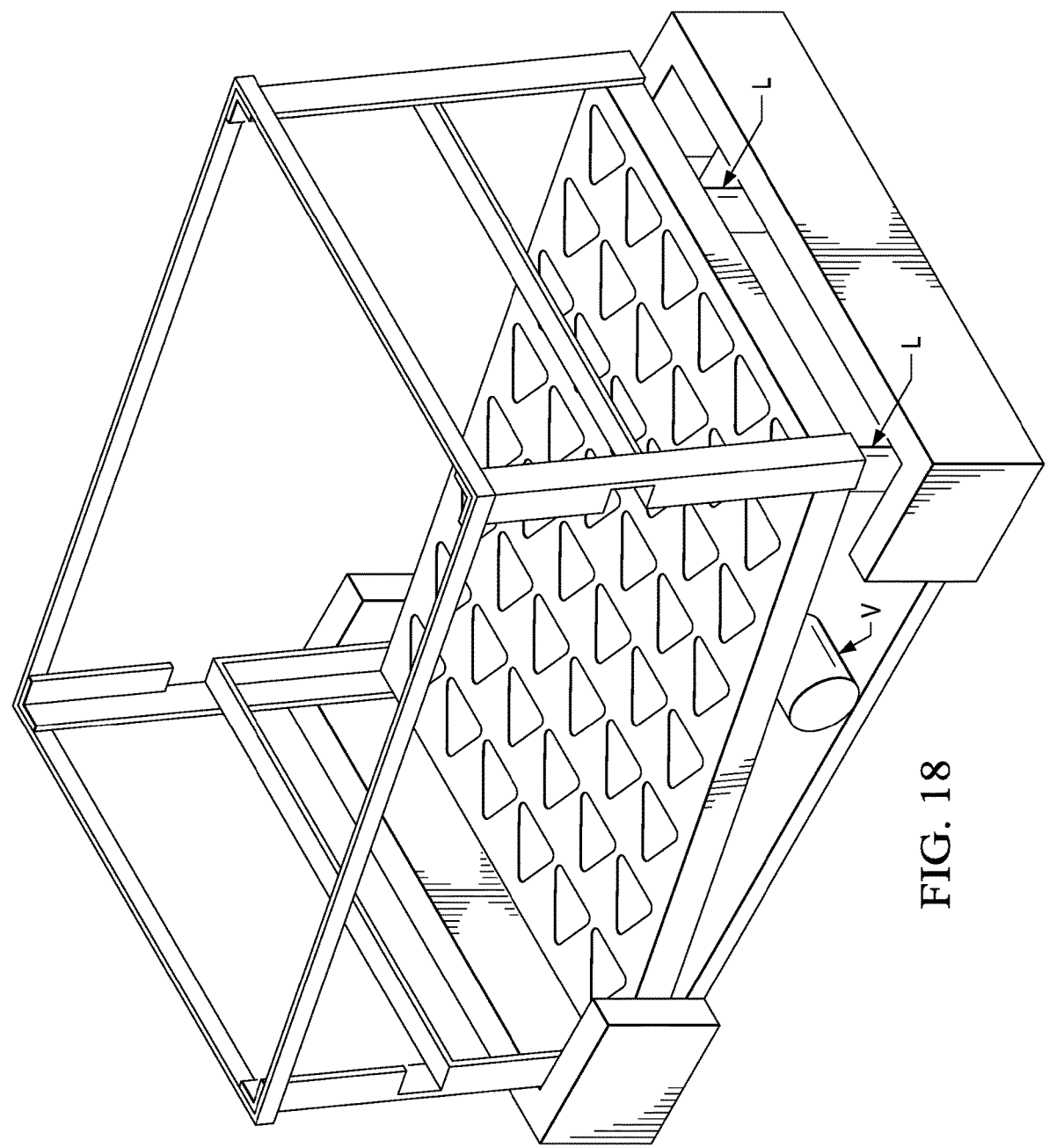
FIG. 18. Multiplate stacker, wherein the frame continues upwards and ledges are provided for the plates to sit on. This embodiment shows only a single ledge, but multiple ledges could be provided.

FIG. 2 shows a prototype single plate stand for a tilt application, wherein a frame holds the plate, and a simple mechanism lifts the plate, and another mechanism vibrates the plate. FIG. 18 is similar, but the frame has additional shelves (in this case 1) for holding additional plates. The shelves are separated sufficiently to allow the full tilt. FIG. 4 shows a prototype single plate that is tilted in two axes. FIGS. 6 and 8 show stands and microtitre plates with different vertex shapes and FIGS. 10-11 show more exemplary well shapes. FIG. 17 displays a multichannel configuration that allows all the channels to be combined.

Figure 3:
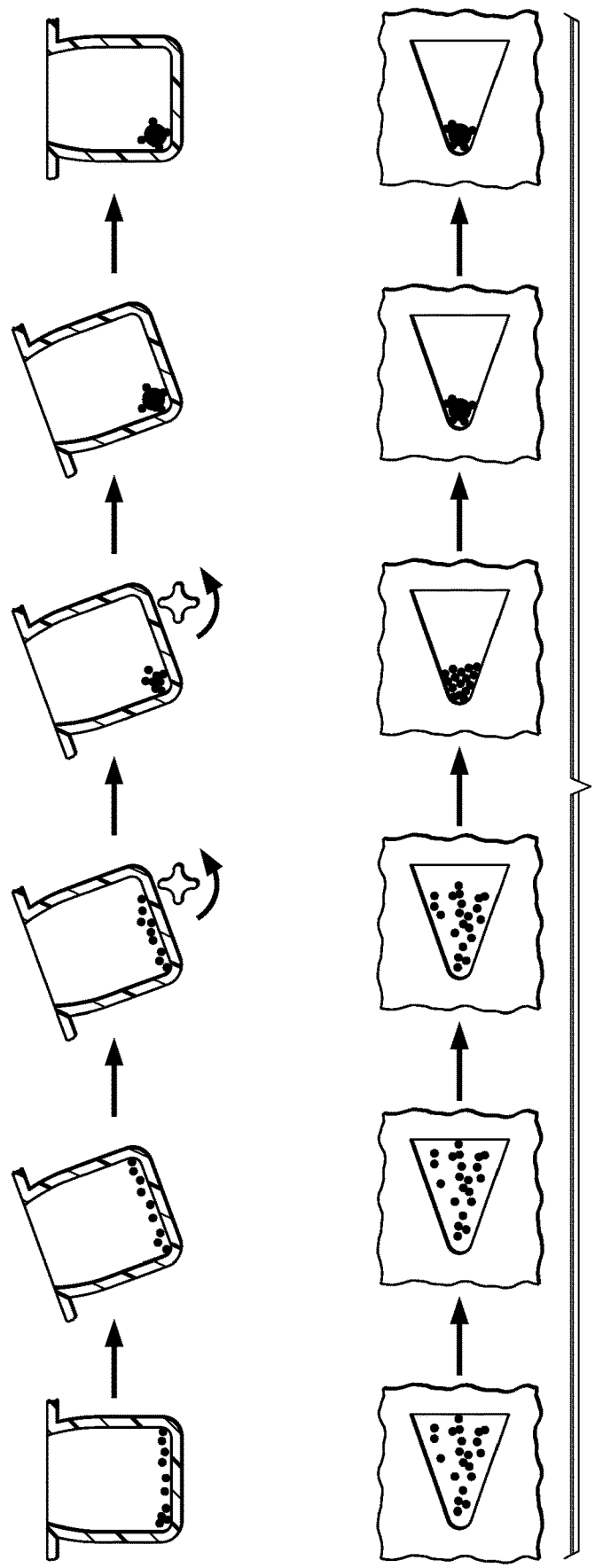
FIG. 3. Side and top views of wells and cells travelling down incline to rest in vertex. Speed of settling is aided with a gentle vibration (0.1-400 Hz, preferably 1-120 Hz, 0.05-4 N, preferably 0.1-0.5 N).
Figure 5:
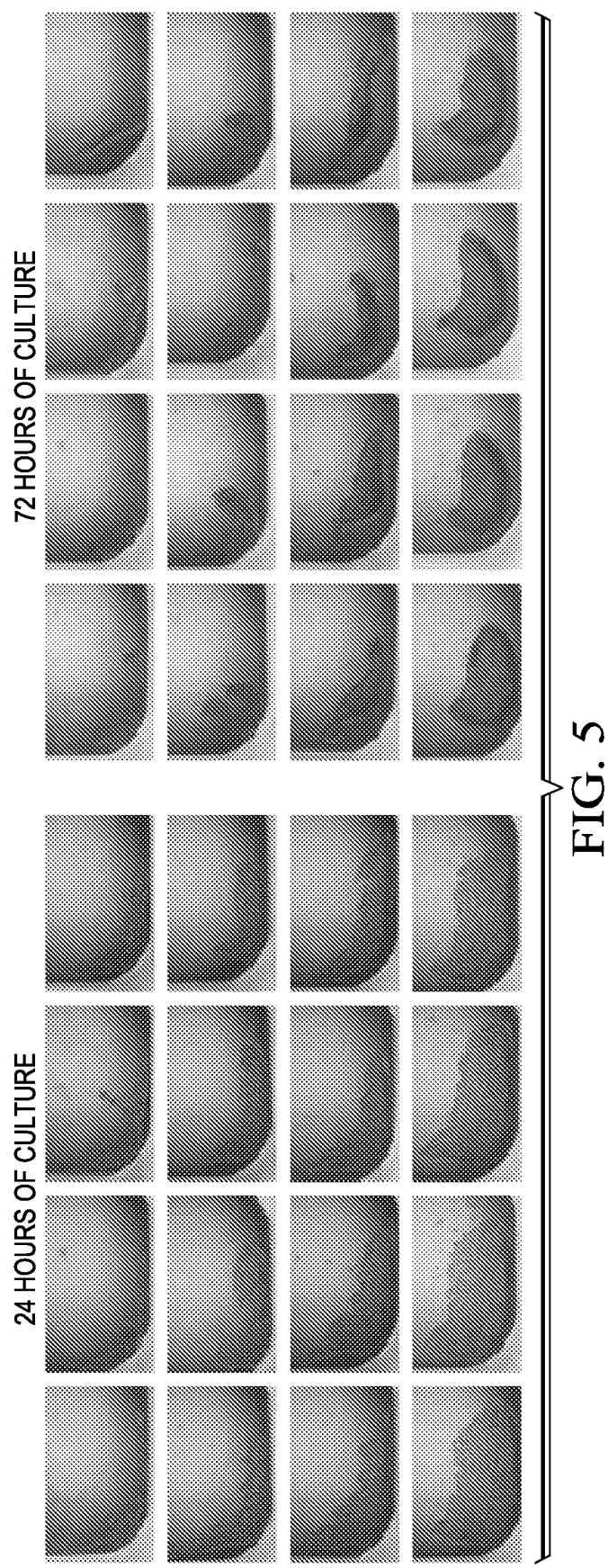
FIG. 5 Actual example of cells collected at the bottom of each well of a plate using vibration and a double incline tilt.
Figure 7:
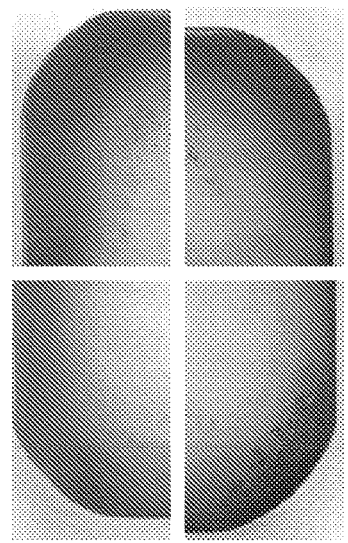
FIG. 7. Stand together with magnetic lid under with magnets placed at the vertex and microtitre plate having square wells with rounded corners (only corners shown).

FIG. 3 shows the top and side views of a well as the cell travels down the side into the vertex. FIGS. 5 and 7 show an actual example of collected cells.

Figure 12:
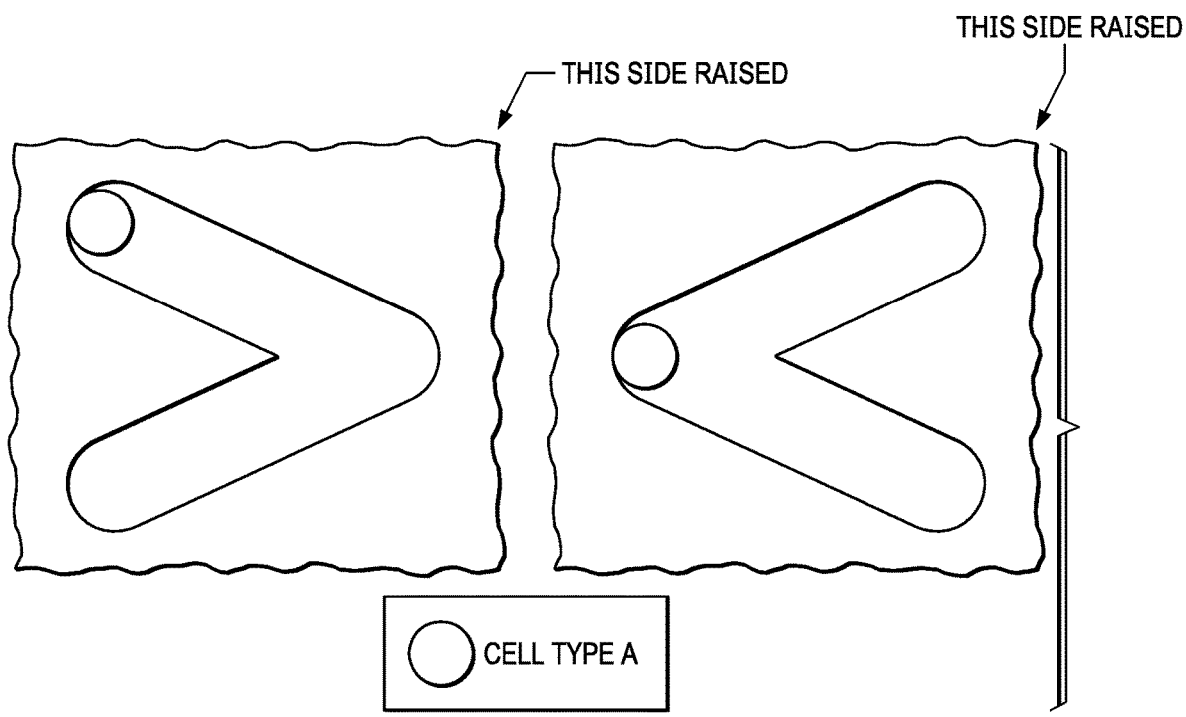
FIG. 12. Various applications for v-shaped wells.
Figure 13:
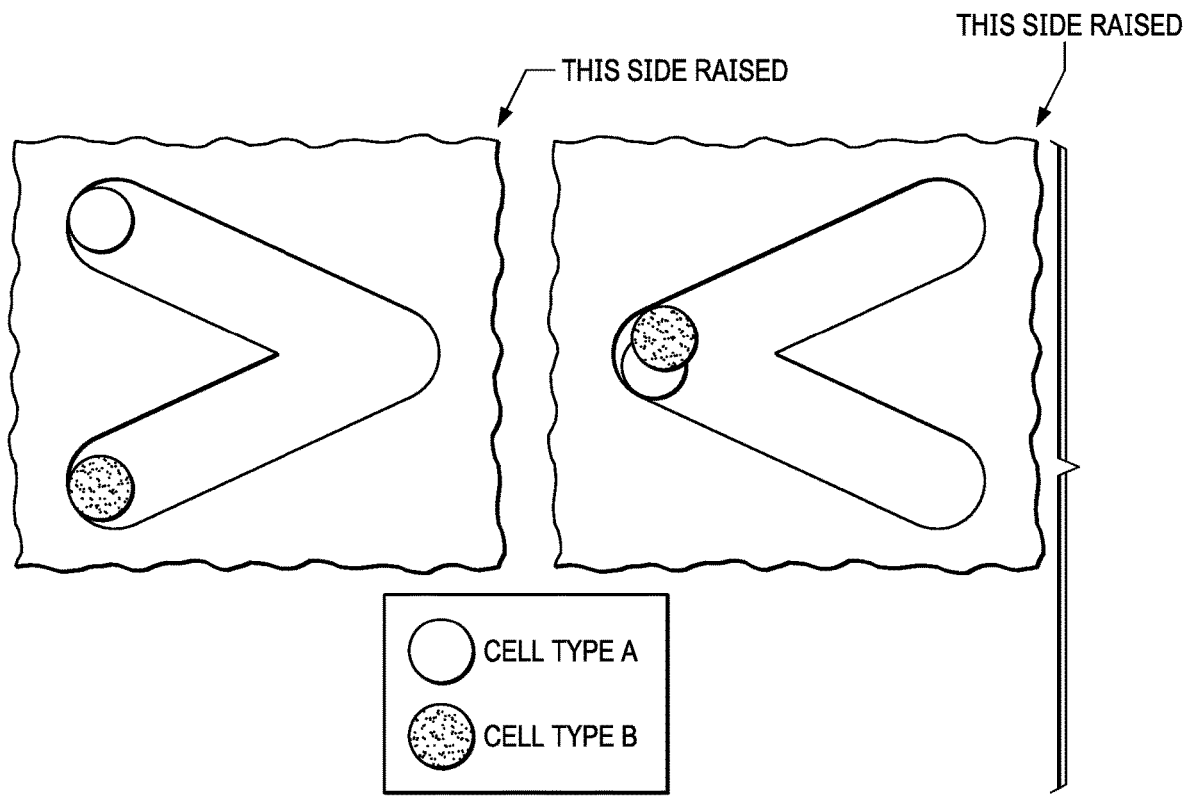
FIG. 13. Co-culturing application for v-shaped wells.
Figure 14:
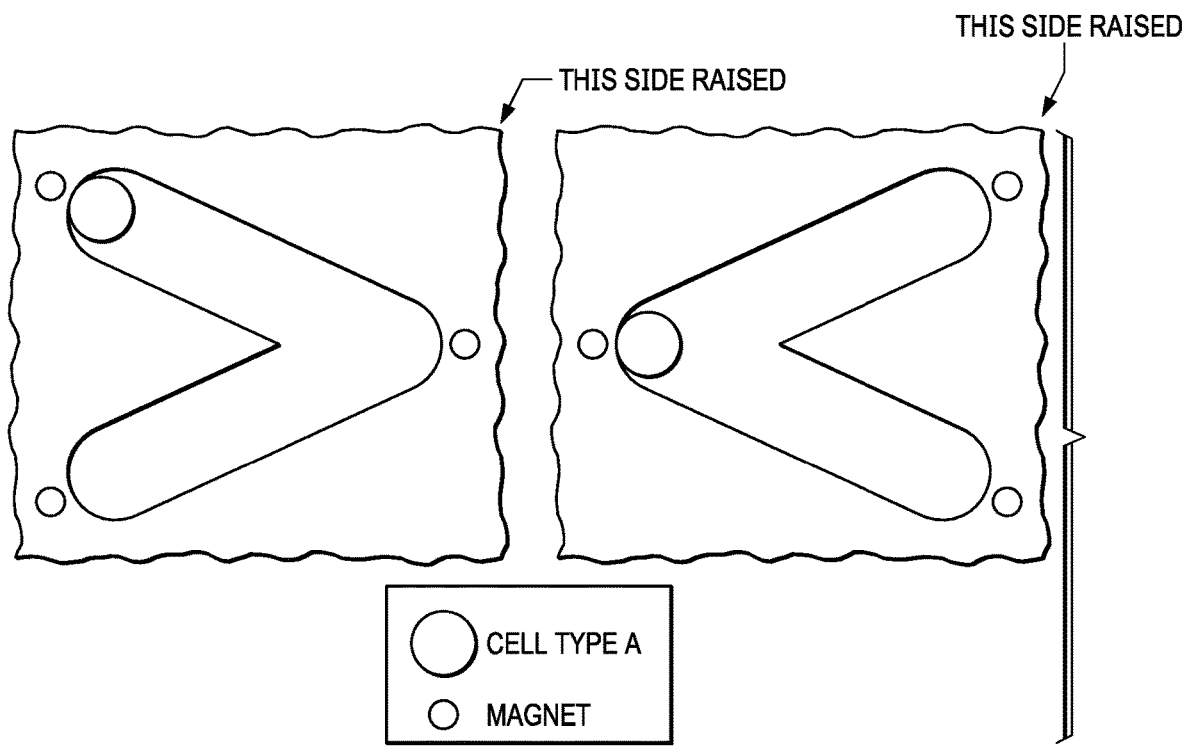
FIG. 14. V-shaped well applications with magnets.
Figure 15:
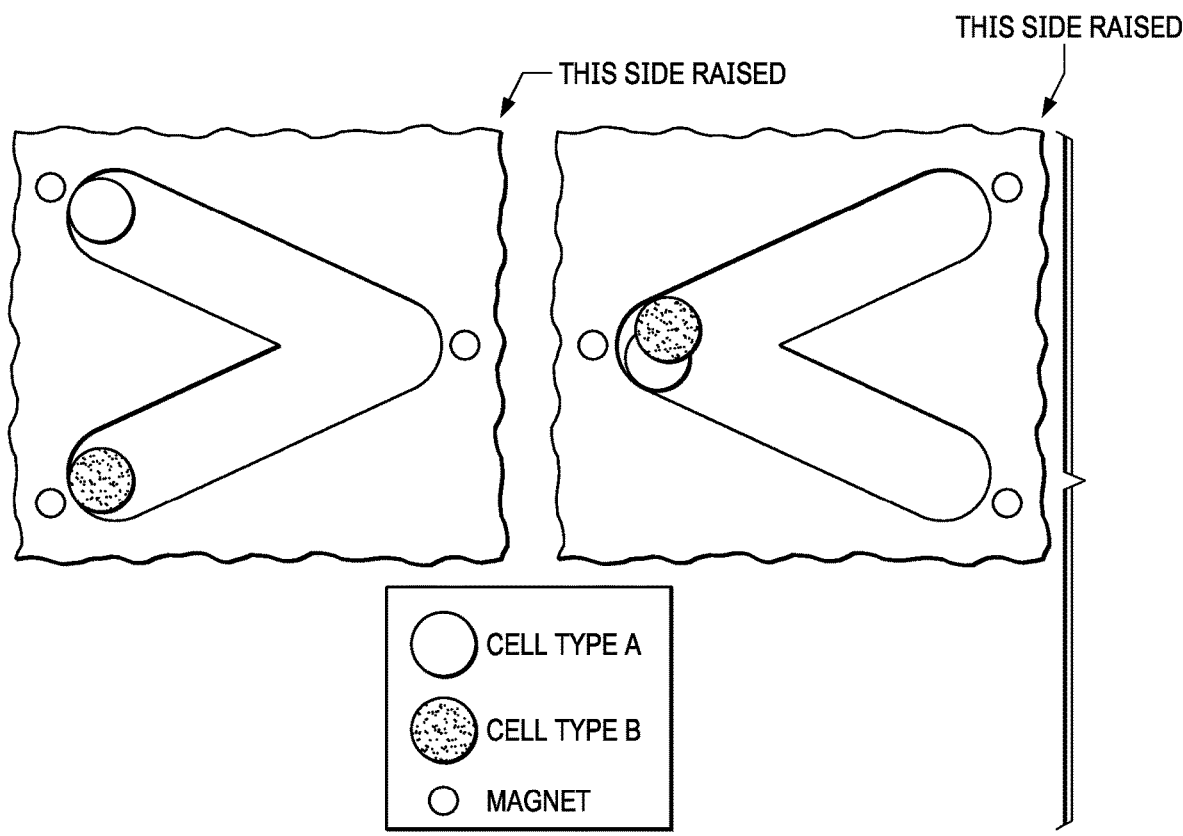
FIG. 15. Co-culturing in V-shaped well with magnets.
Figure 16:
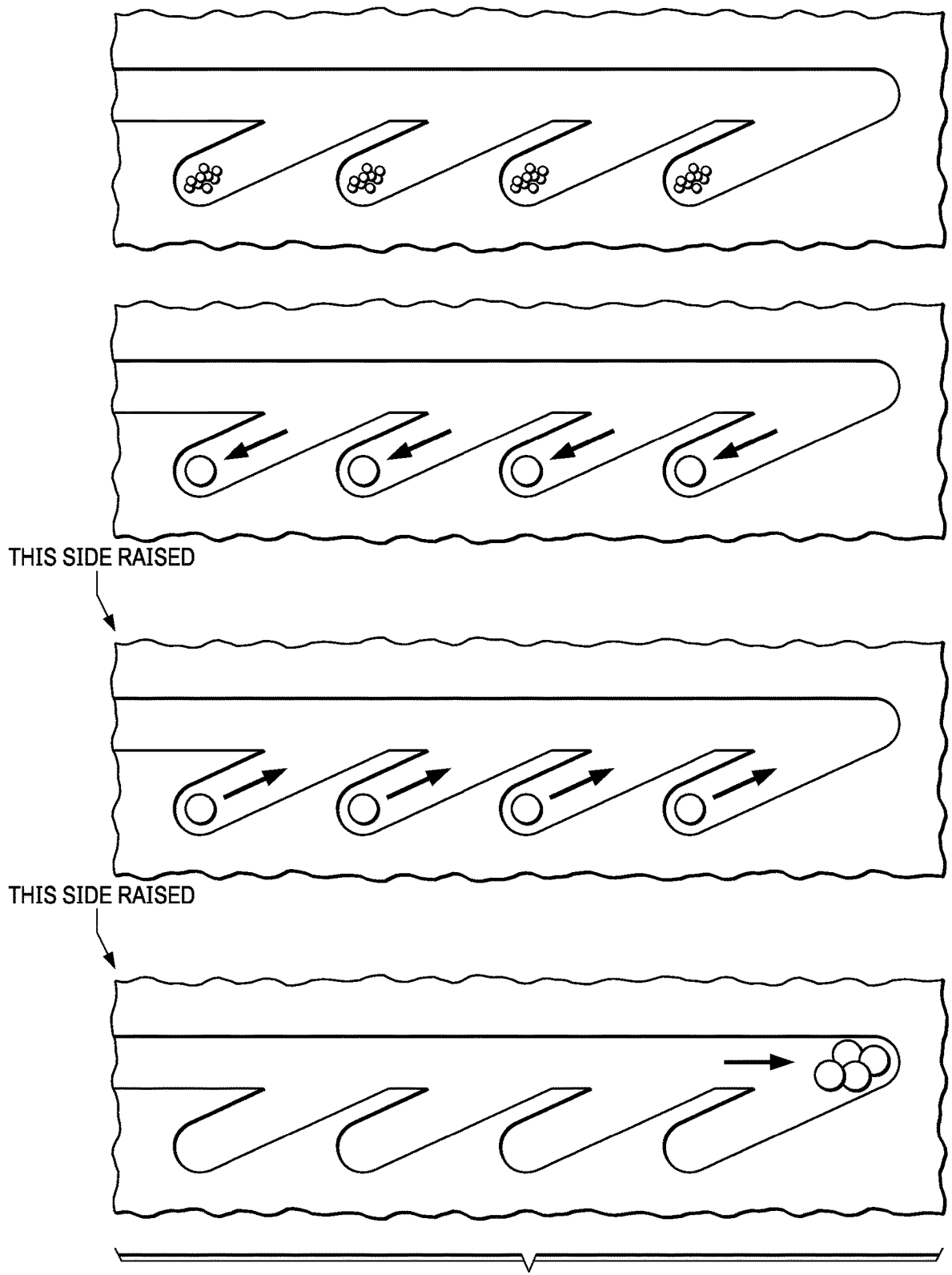
FIG. 16. Multichannel well and application, arrows showing movement of cell mass caused by lifted the appropriate side.

FIG. 13 showed the cross section of a "V-shaped" well. A V-shaped well may be very beneficial in certain applications such as media exchange and co-culture of different cell types. FIGS. 12 and 14-15 show various applications of such wells. The cells of different types can be placed each of the legs of the V, thus allowing them to culture in the same media solution but not in direct contact. Further, by tilting the plate so the lowest point of the well is the "bottom" of the "V", where the legs of the V come together, the different cell types can be brought together to be co-cultured in direct contact. This could be desirable with a variety of cell types and applications, including but not limited to culturing stem-cells, immune cells, circulating tumor cells, cells from liquid and solid biopsy samples, bacterial cells.

In use, the magnetic drivers are used with cell culture plates to levitate cells. First the cells are magnetized, e.g., using NanoShuttle™ (Nano3D BioSciences, TX). NanoShuttle™ is a nanoparticle assembly (~50 nm) consisting of gold, iron oxide, and poly-L-lysine. The poly-L-lysine will non-specifically bind to cell membranes via electrostatic interactions. NanoShuttle™-PL will be retained by the cells for roughly 8 days, after which they are released into the extracellular space. If in 3D, NanoShuttle™-PL will be released into the extracellular matrix, and the 3D culture will retain its magnetic nature. These magnetized cells require magnetic forces (30 pN) only strong enough to aggregate, but not harm cells. Further NanoShuttle™ has been demonstrated to not effect cell proliferation, viability, metabolism, inflammatory or oxidative stress responses, phenotype, and other macro cell functions.

Cells are magnetized by adding NanoShuttle™-PL directly to a flask of cells that is 70-80% confluent, and incubating overnight. Typically, NanoShuttle™-PL is added typically at a concentration of 1 μL/10,000 cells. The next day, treated cells are enzymatically detached with trypsin and resuspended in suitable media. Cells can also be magnetized in suspension. Briefly, suspension cells are magnetized by mixing them with NanoShuttle™-PL for ~30 min on a gently rotating orbital shaker. The cells are collected, e.g., by centrifugation, resuspended in suitable media and ready for use.

The cells need to take up enough magnetic nanoparticle so as to be levitated in the magnetic field, but not so much as to disrupt the cells normal metabolism. Levels of about 30-150 pg/cell, or about 50 pg of magnetic iron oxide are typical.

Once magnetized, the cells can be levitated for assembly, by adding magnetized cells to a plate, preferably a flat-bottom, ultra-low-attachment plate for maximum levitation efficiency, but having the triangular cross-sections described herein. A magnetic drive as described herein is then placed under the cell culture plate. Cell assembly typically begins in minutes, and is complete in hours, although different cell types will require different times, and this is typically optimized before an experiment is begun. If desired, the magnetic drive can be left in place even after the cells have assembled into a stable 3D culture. However, typically the drive is removed and the cells studied further. Typically, the cells retain their 3D structure once stabilized for about 4-8 hrs in the magnetic field.

One or more drugs or other agents can be added to the 3D cultures, and then the 3D cultures can be imaged by removing the magnets and tilting the plates so as to collect the 3D cultures at the vertex. The wedge is then carefully removed, and the plate photographed through the base. Photography or other imaging will be faster and more reliable because the cells are at a known location and depth and a single camera shot can visualize every well in the plate at the same time.

Figure 9A:
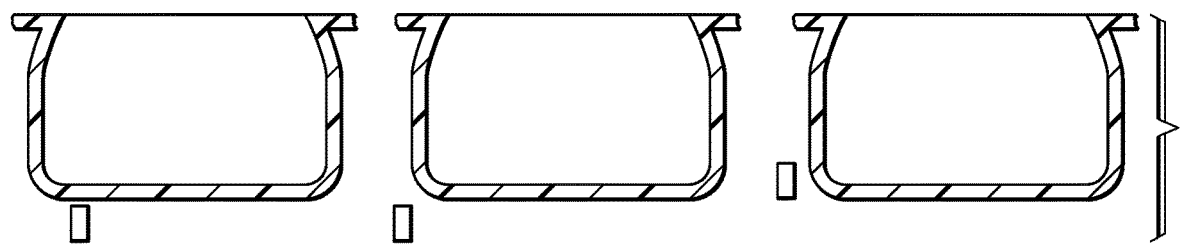
FIG. 9A. Side view of preferred positions for magnets for use in tilt applications. For non-tilt applications, the magnets are positioned to be directly over or under the well, but in tilt applications, the magnets should be at, adjacent, or at the side of one vertex of the well.

If desired the magnetic drive can also be used to collect cells and/or exchange media, in which a variant drive is provided with the magnets positioned over/under the vertex, rather that the center of the well. See FIG. 9A. Different magnetic lids can be made for these two purposes, or a single lid can be made with a small amount of additional space (½-1× well width) on one edge, and then the magnets are positioned centrally or to one side of the wells by shifting the position of the lid to one side or the other. This can also be integrated as part of a scanning microscope where individual wells are visualized.

Figure 9B:
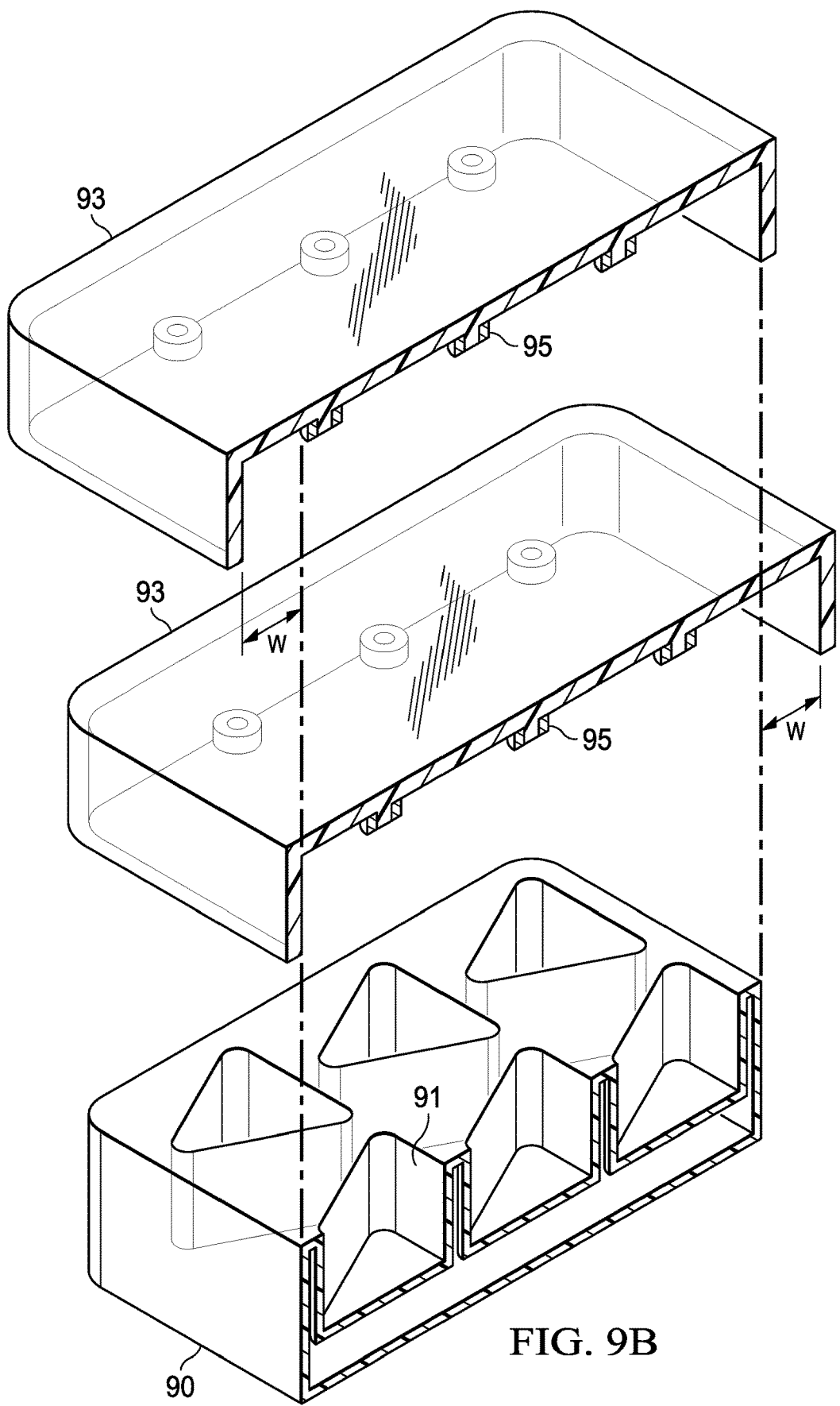
FIG. 9B cross section of plate having triangular wells and magnetic lid with extra space -W- on one side, allowing the magnets to site centered or to one side of the wells, depending on which lid edge is pushed against plate edge.

This is shown in FIG. 9B, which shows a cross section through a plate 90 with triangular wells 91. Above that hovers a cross section of a lid 93 with magnets 95. Lid 91 has an extra space W on one side, which is 0.5-1× well 91 in width. Thus, pushing the lid to the right centers the magnets 95 over the wells 91, whereas pushing it to the left moves the magnets 95 about 0.5-1× well width off center. The lid can also be labeled (not shown) to indicate which side should rest against the edge of the plate. The plate doesn't move too far to the left because the rim of the lid meets the side of the plate, and movement is stopped.

We have shown a simple wedge used for tilting the cells, and this has the advantage of being very inexpensive. However, more sophisticated mechanisms can be used as well. For example, the plates can be set in a stand that holds multiple plates (FIG. 19), and the entire stand can tilt, tilting every plate at the same time. This can be done with a screw foot or feet, extending or telescoping leg or legs, a lever or the stand lift can be motor driven. A modified lid could also be used/combined to facilitate stacking the plates while they are tilted and stacked vertically.

A motor driven stand would be preferred for high throughput applications, as allowing a steady slow lift and return to level with minimal sloshing of media or movements of cells. The stand can also be sized so as to allow a camera or other imaging means to fit under the plates for the photography, thus minimizing any plate motion. Ideally, the stand will have shelves for sliding in the plates as described in US20150091233, and the imager will fit in underneath and can shoot a plurality of plates at one time.

Figure 19A:
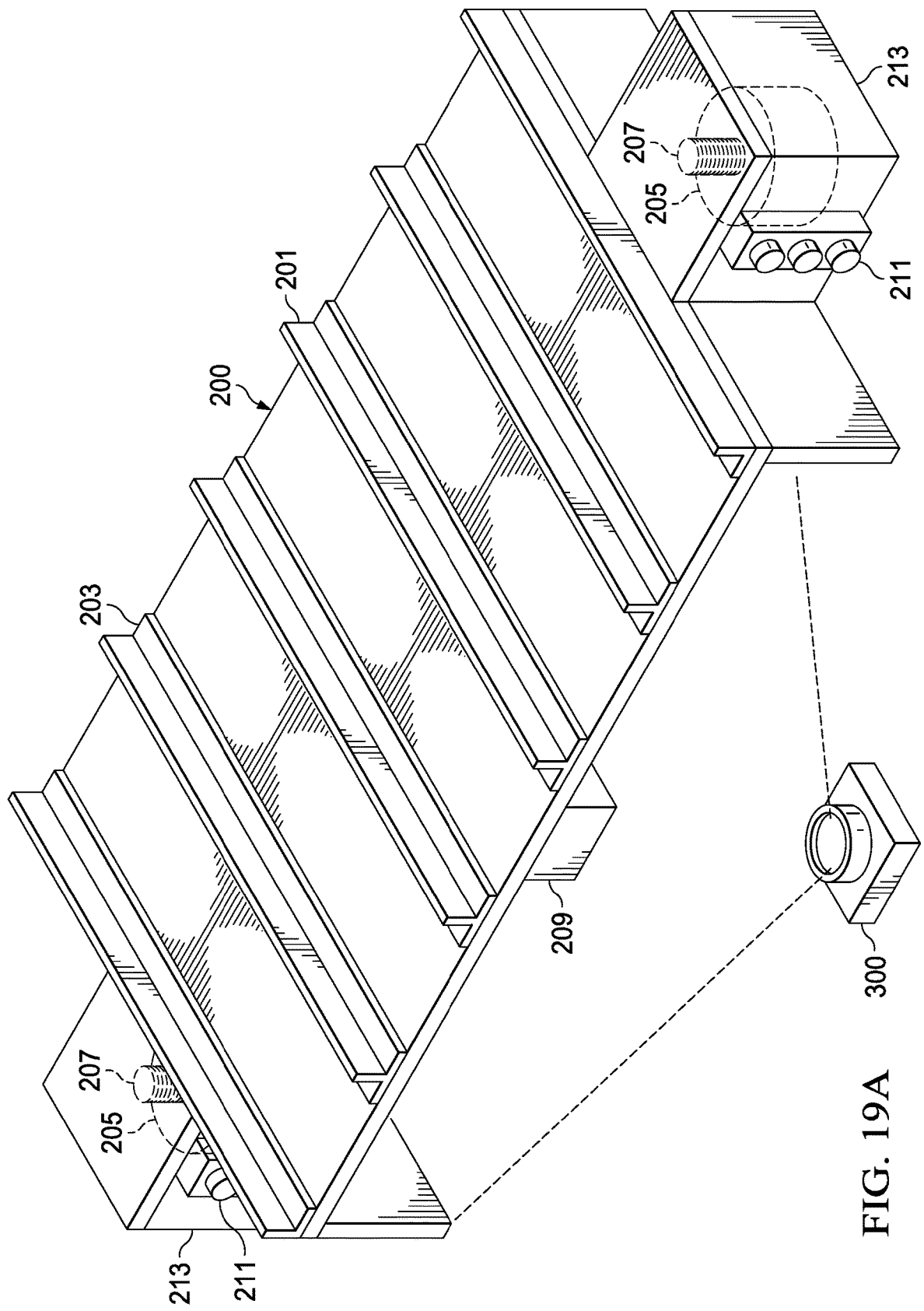
FIG. 19A-B. A single level multiplate tilting stand (A) and as lifted (B), with camera or other imaging modality underneath and able to photograph all plates or image individual wells, as desired.
Figure 19B:
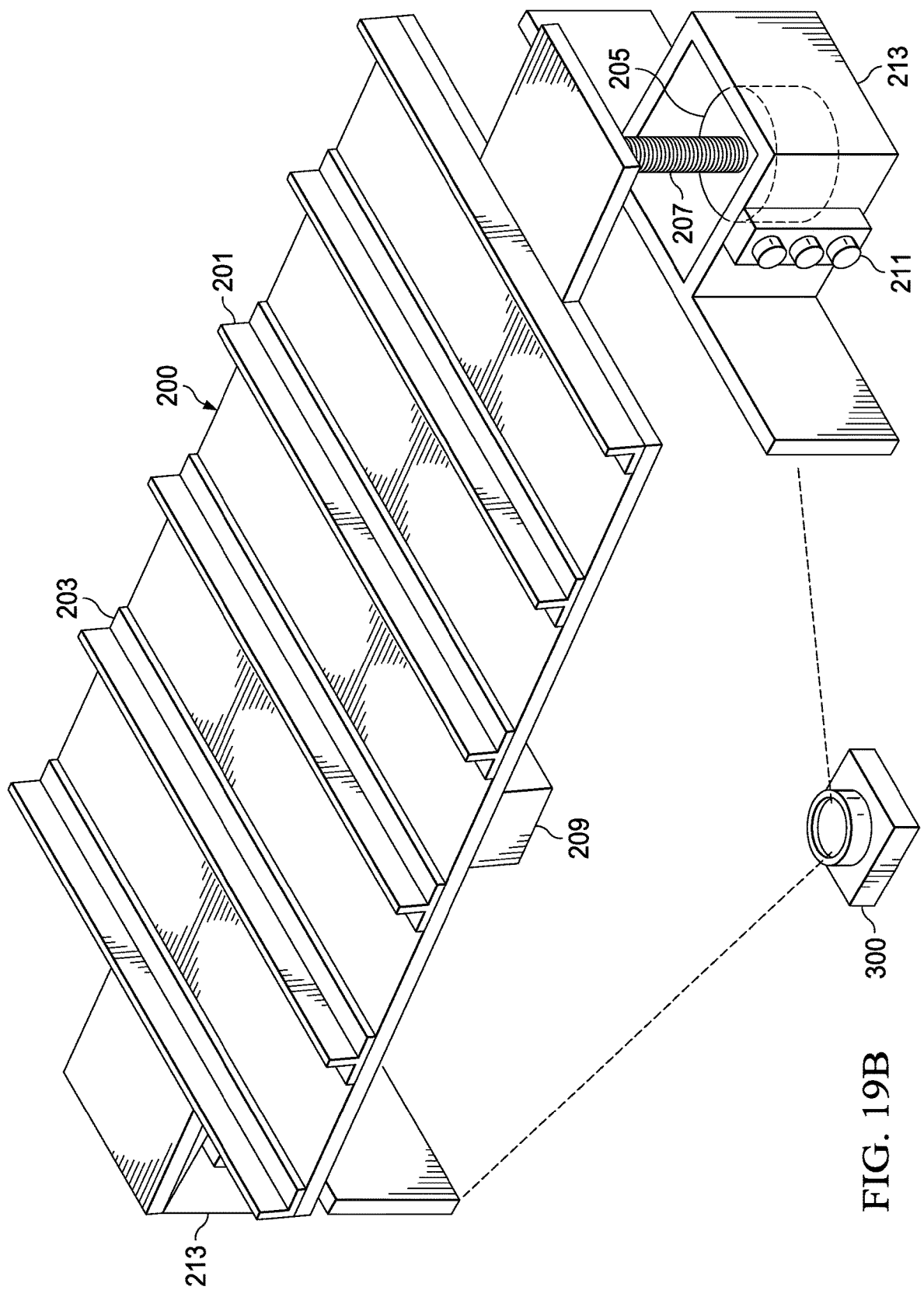

A multiplate automated tilter is provided in FIG. 19A. A multiplate motorized tilter stand having a base 200 over a housing 213 which houses motors 205 and 209 and provides controller panel 211. The base is merely a framework, having walls 201 to prevent plates from sliding off, and ledges or shelves 203 to support plates. Inside the housings 213, motors 205 provide mechanized lift via lift mechanism 207. Vibrating motor 209 can be mounted in the center of the housing, on the under-side of the base 200 to convey vibration to the base, and thereby to the plates positioned thereon. However, it can be mounted at other locations too, provided it does not interfere with imager or camera 300, e.g., an outer edge. FIG. 19B shows the device after lifting via motors 205.

We have shown a pair of motors and a pair of housings for same, as this will allow a very large stand to be made and provide lift at both corners of a stand. However, smaller stands may need only a single motor set. Where double lifters are provided, they will typically be controlled by the same circuitry, thus saving on cost of manufacture. However, this is not essential, and dual circuitry would allow the double axes tilt described above.

Figure 20A:
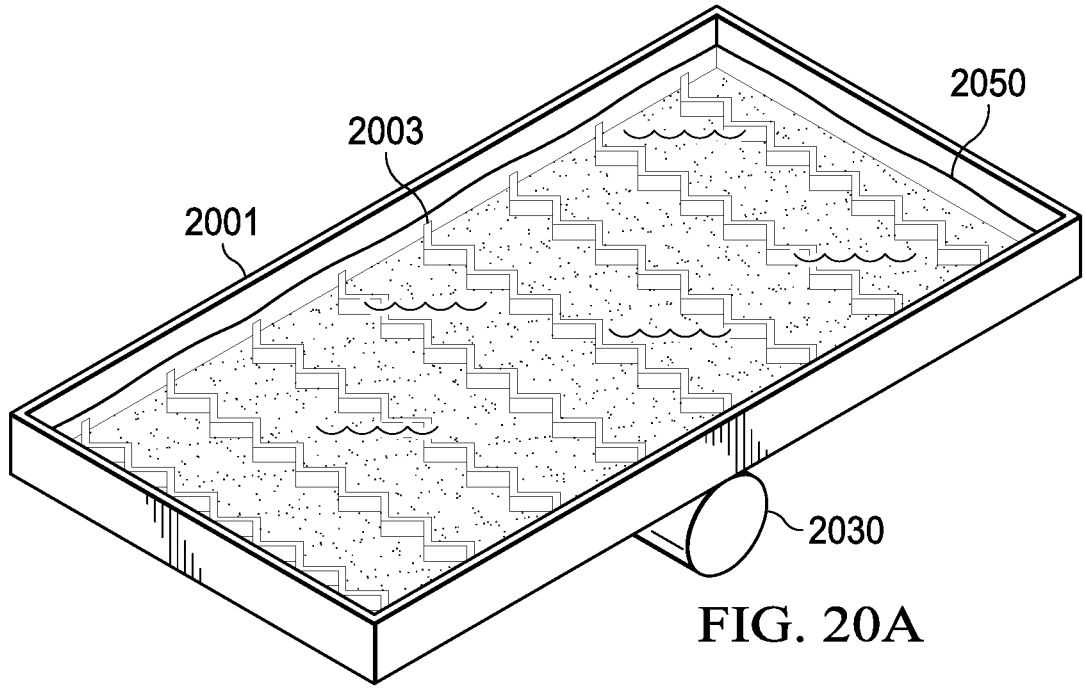
FIG. 20A-C are perspective views of a plate designed with multiple vertices inside a single large well, allowing many 3D cultures to be formed, one at each vertex.
Figure 20B:
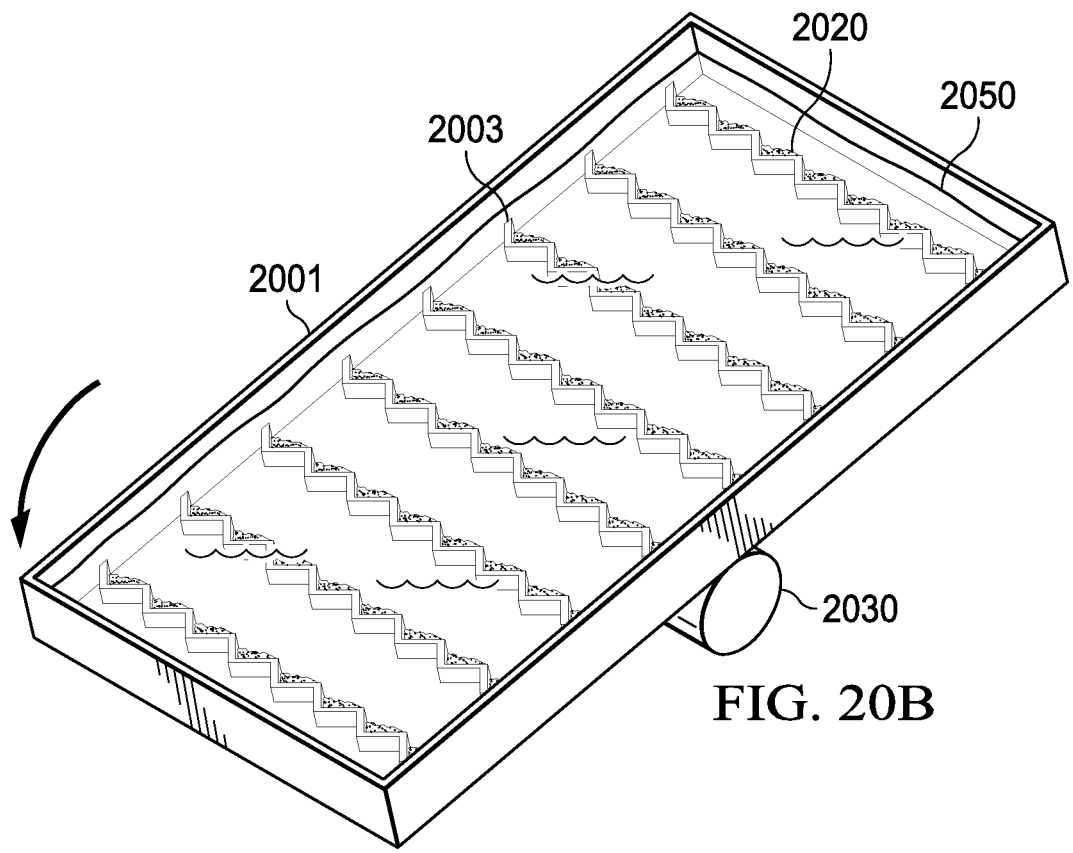
Figure 20C:
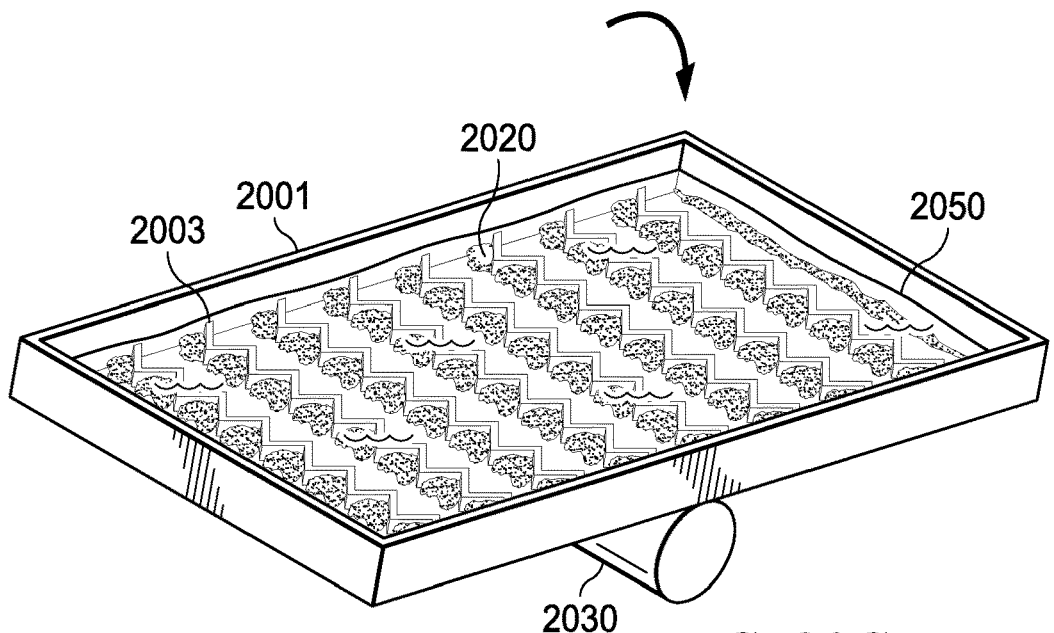

FIG. 20A shows another variation of a plate that can create a large number of cell clumps or spheroids for research uses. There is a single large well—in this case rectangular and preferably of the same size and dimensions as a standard microtiter plate. Inside the exterior walls 2001 are shorter, zigzag cell sorting walls 2003, which can be arranged in any pattern, but here shown arranged in parallel lines and traversing from one side to the other. Since the sorting walls 2003 are shorter than the exterior wall 2001, when medium containing cells 2050 is added to a depth greater than the sorting walls 2003, and the plate is rocked back and forth on rocker 2030, the forces will cause the cells 2020 to begin to collect in the vertices. See FIG. 20B. Once collected, the rocking can be discontinued, and with culture time, each of the cells 2020 in the vertices will grow, creating a 3D spheroids or clumps. FIG. 20C.

Figure 21A:
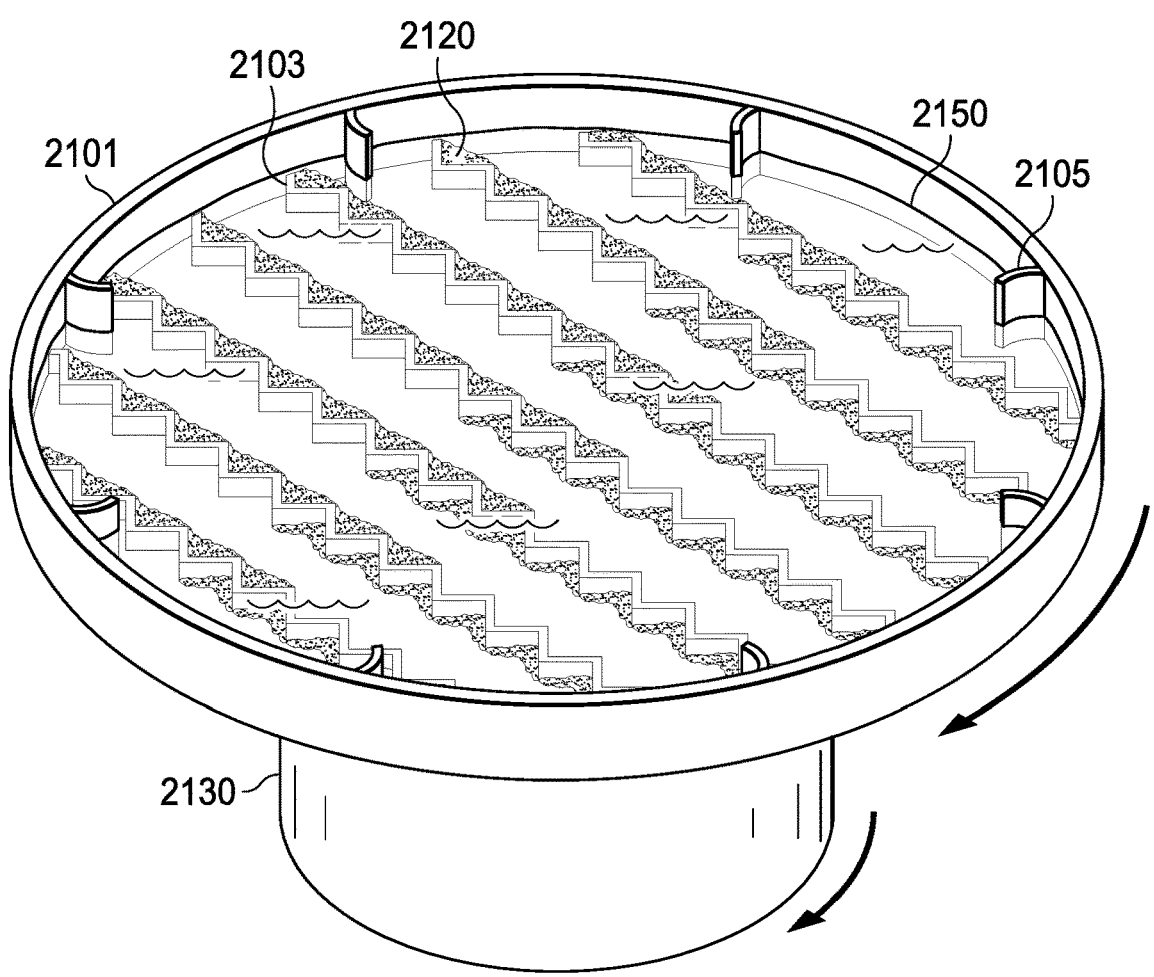
FIG. 21 shows yet another variation on the idea of FIG. 20, wherein the larger well is circular, and the plate is rotated. Cells will of course, be directed to the edge of the plate by centripetal forces during rotation, but the curved walls will redirect cells back towards the center of the plate, where they will again be collected in the vertices.
Figure 21B:
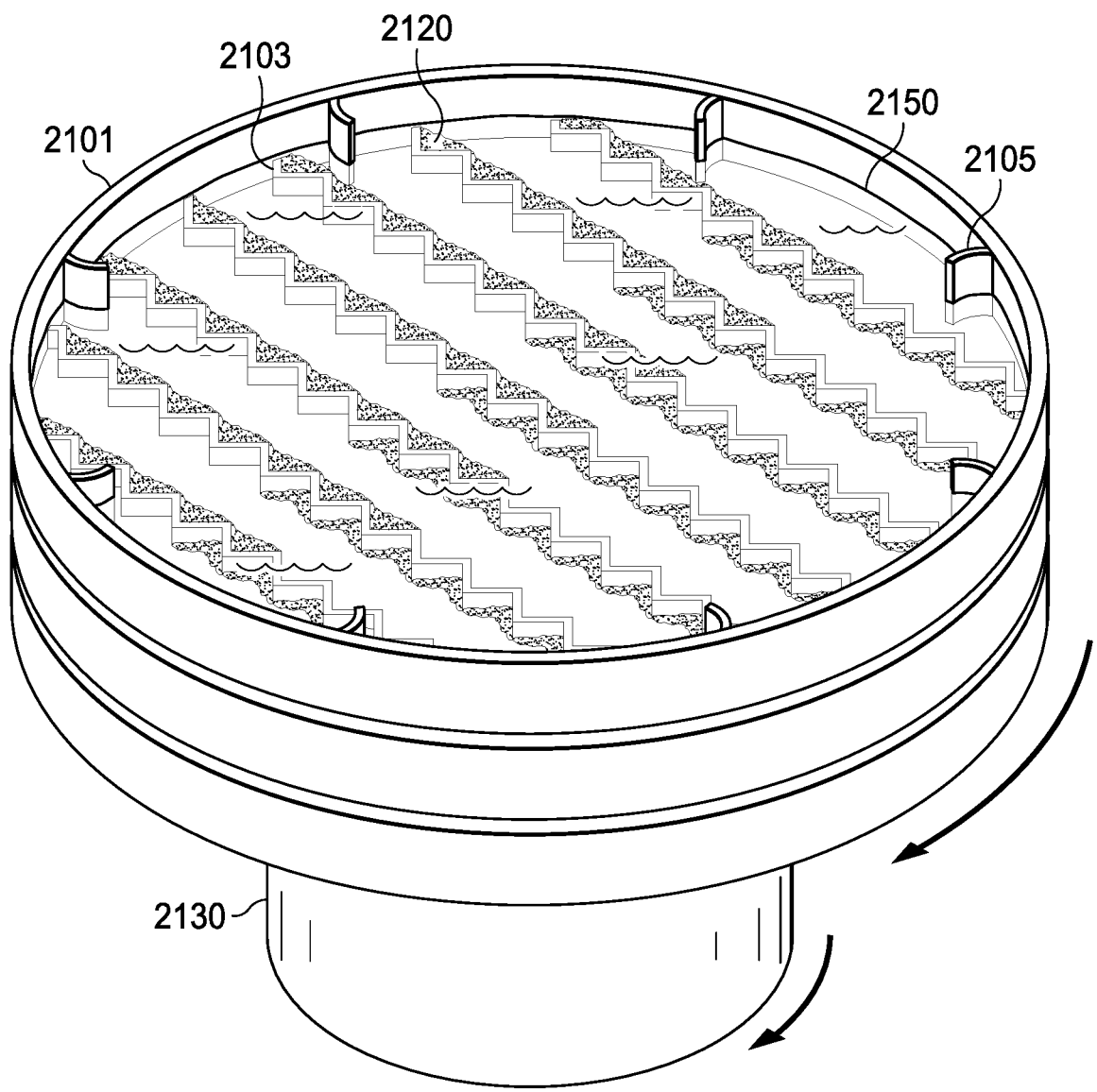

FIG. 21 has another variation on this idea, wherein the well is circular, again having the taller exterior wall 2101 and plurality of zigzag circular walls 2103. Also included are curved walls 2105 extending from the exterior wall 2101 and projecting a short way into the well diameter. These curved walls 2105 will direct medium and cell 2150 back towards the center of the plate, thus preventing all the cells from ending up on the outermost edge. As before, when rotation is stopped, the cells will grow and clumps will form (not shown).

Figure 22:
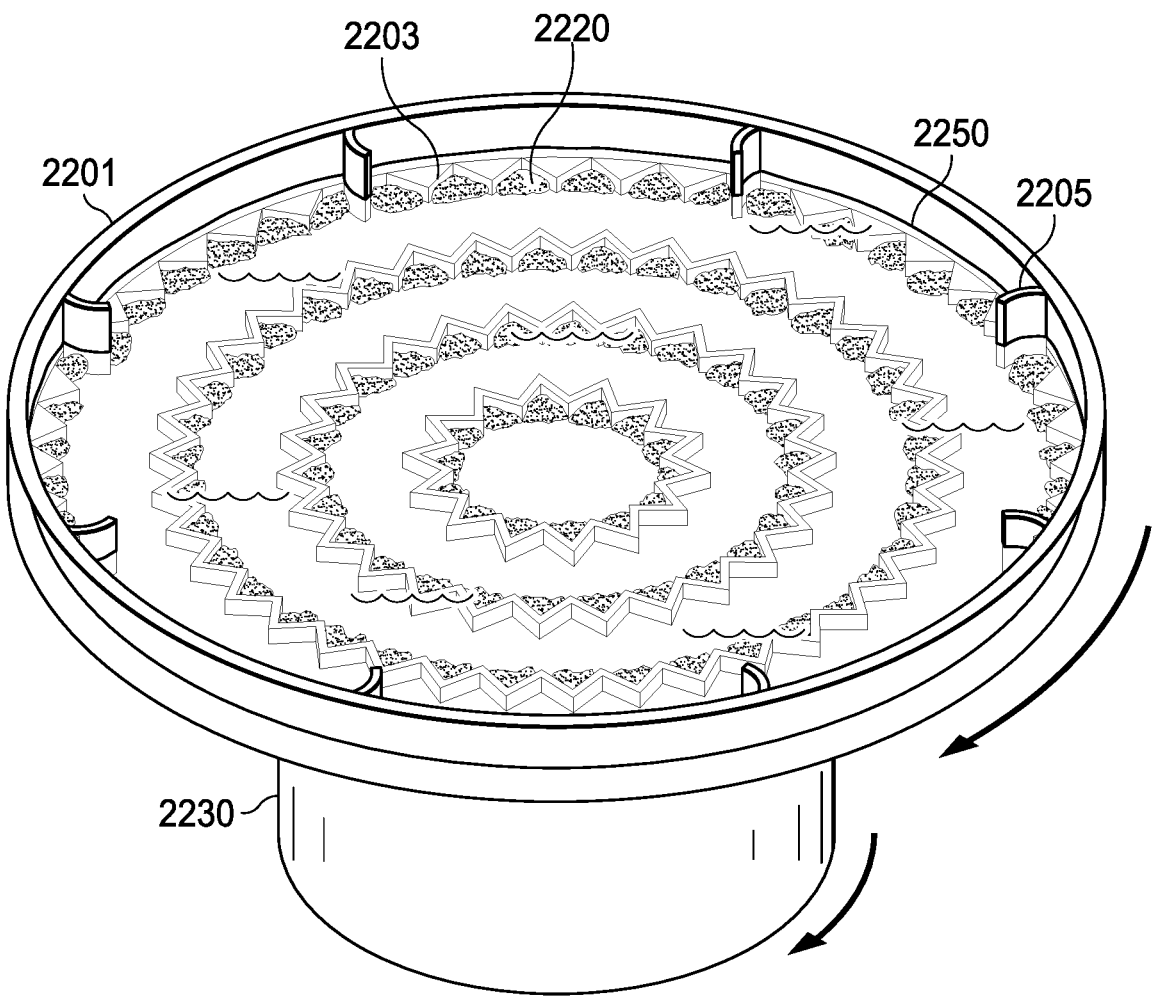
FIG. 22 shows another embodiment, with concentric zigzag sorting walls, to better take advantage of the centripetal forces created by rotating the plate. Here, the cells collect in the V's that open to the center of the plate/axis of rotation.

FIG. 22 has yet another variation, wherein the zigzag sorting walls 2203 are arranged in concentric rings about the center of the plate. This allows maximum beneficial use of the centripetal forces. The curved walls 2205 and exterior wall 2201 have the same function as in FIG. 21.

Figure 23:
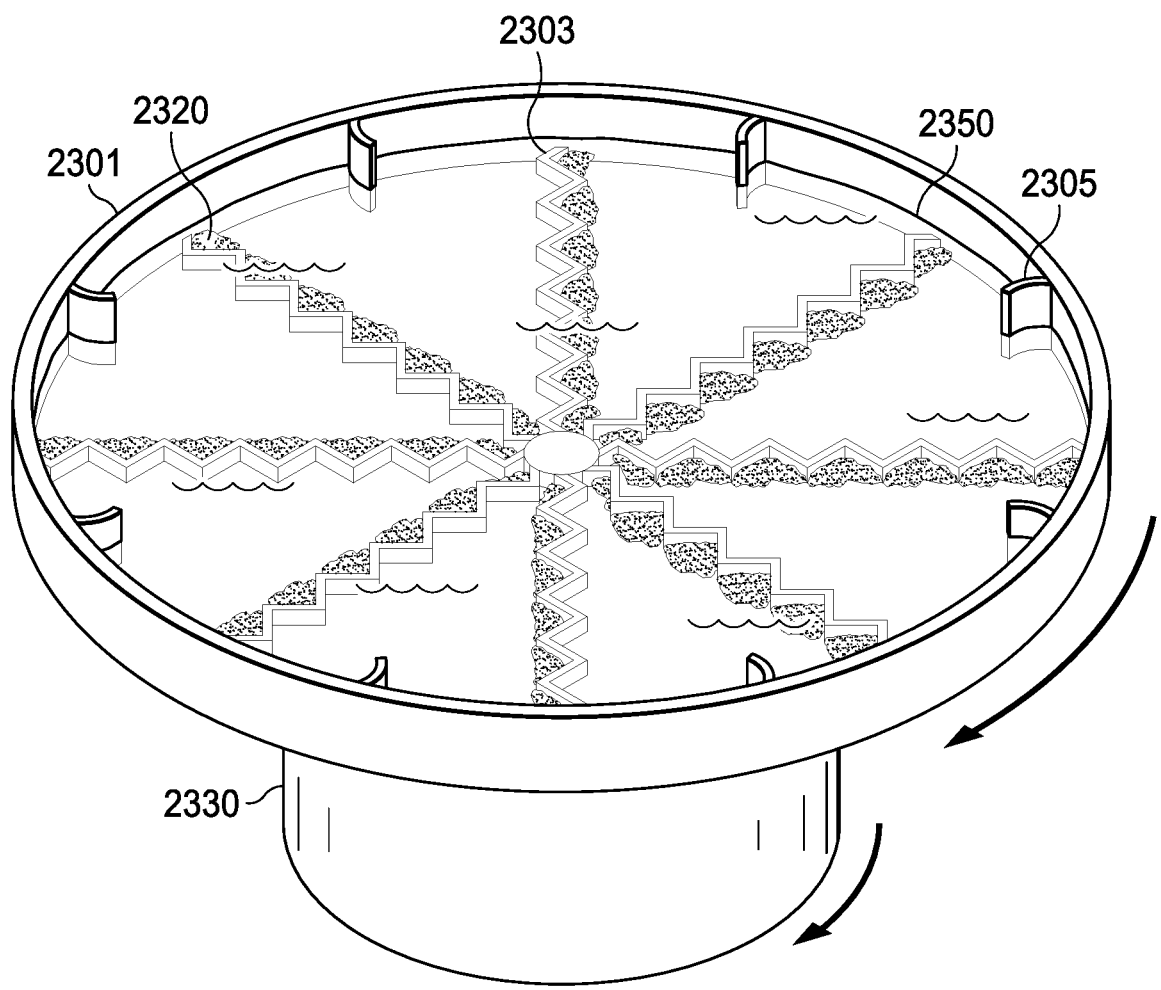
FIG. 23 shows yet another embodiment, with radial zigzag sorting walls.

FIG. 23 has still another variation, wherein the zigzag sorting walls 2303 are arranged radially from the center of the plate. The curved walls 2305 and exterior wall 2301 have the same function as in FIG. 21.

FIG. 24A-E show top and side views of a 384-well plate according to the present invention as well as a cross section, wherein each well of the 384-well plate has a triangular cross section in top view. Furthermore, an enlarged view of the plate is shown illustrating that a vertex of each individual well has rounded corner oriented to a short side of the plate.

Figure 25A:
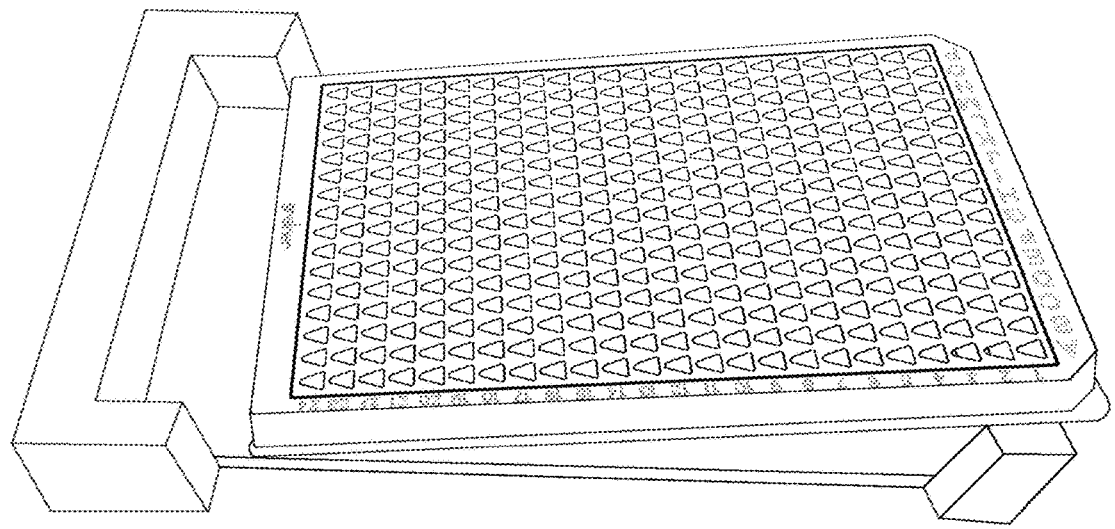
FIG. 25A-C. Simple three-dimensional print of a 384-well plate in a plate stand for tilt application, in high perspective (A), low perspective (B) and top (C) views, each well of the 384-well plate having a triangular cross section.
Figure 25B:
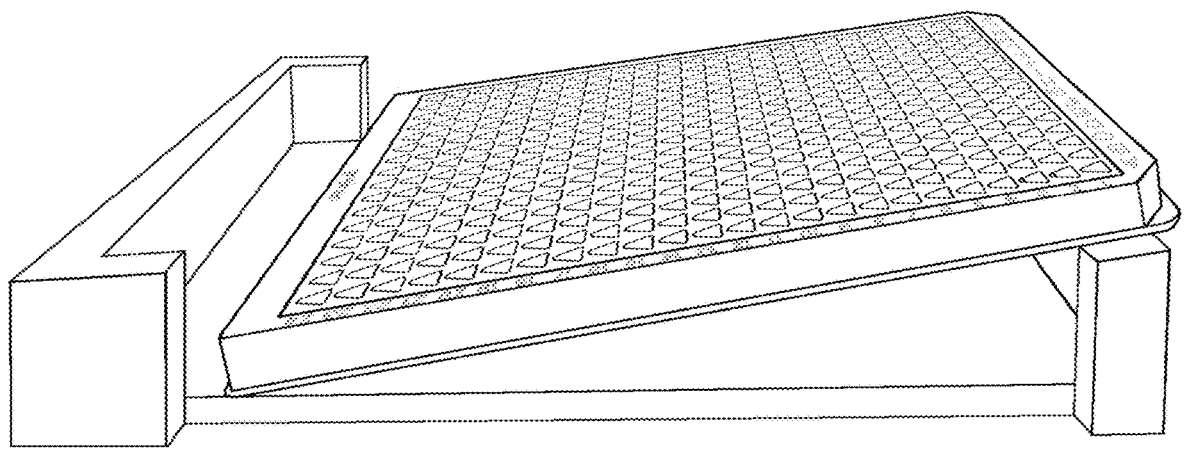
Figure 25C:
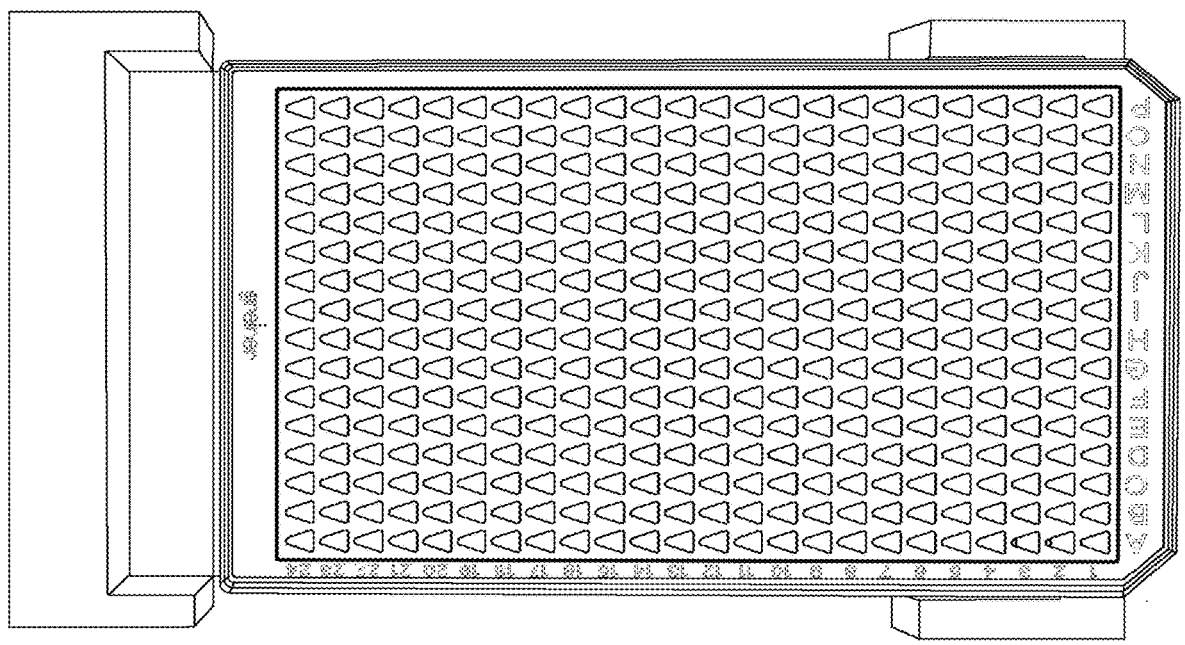

A simple three-dimensional print of the plate shown in FIG. 24 in a plate stand for a tilt application as shown in FIGS. 2, 4, 6 and 18 is provided in FIGS. 25A-C.

The present invention further pertains to following aspects:

1. A multiwell culture plate, comprising: a rectangular plate having a first and second long side and a first and second short side; said plate having a plurality of wells; and, each of said plurality of wells having a non-circular cross section having at least one vertex when viewed from a top view; and each of said wells having a flat transparent base lacking any obstruction, such that the entirety of the well contents can be imaged from underneath the base.

2. The multiwell culture plate of aspect 1, said vertex oriented to said first long side.

3. The multiwell culture plate of aspect 2, further comprising a rectangular wedge that fits under said rectangular cell culture vessel thus lifting said second long side by 15-45°.

4. The multiwell culture plate of aspect 1, said vertex oriented to said first short side.

5. The multiwell culture plate of aspect 4, further comprising a rectangular wedge that fits under said rectangular cell culture vessel thus lifting said second short side by 15-45°.

6. The multiwell culture plate of aspect 1-5, said vertex having a rounded corner.

7. The multiwell culture plate of aspect 1, further comprising a rectangular cap having a lip around an outer circumference thereof and being shaped to fit over or under said multiwell culture plate.

8. The multiwell culture plate of aspect 1, further comprising a rectangular cap having a lip around an outer circumference thereof and being shaped to fit over or under said multiwell culture plate, said cap having a plurality of magnets affixed thereto, thus holding said magnet over each said well when said cap is in place over or under said multiwell culture plate.

9. The multiwell culture plate of aspect 1, further comprising a rectangular cap having a lip around an outer circumference thereof and being shaped to fit over or under said multiwell culture plate, said cap having a plurality of magnets affixed thereto, thus holding said magnet over each said well when said cap is in place over or under said multiwell culture plate, each adjacent magnet being in an opposite polarity.

10. The multiwell culture plate of aspects 8-9, wherein each said magnet sits over each said vertex.

11. The multiwell culture plate of aspects 8-9, wherein each said magnet sits over a center of each well.

12. The multiwell culture plate of aspects 1-11, having 6 wells.

13. The multiwell culture plate of aspects 1-11, having 24 wells.

14. The multiwell culture plate of aspects 1-11, having 96 wells,

15. The multiwell culture plate of aspects 1-11, having 384 wells

16. The multiwell culture plate of aspects 1-11, having 1536 wells.

17. The multiwell culture plate of aspects 1-11, having 3072 wells.

18. The multiwell culture plate of aspects 1-11, having 6144 wells.

19. A method of imaging a cell culture, comprising: incubating one or more cell types in a medium in one or more wells of the multiwell culture plate of aspect 1; tilting said multiwell culture plate so that cells collect at said vertex; optionally vibrating said plate; removing said tilt when all cells have collected at said vertex; and imaging said cells through said flat base.

20. A method of imaging a cell culture, comprising: incubating one or more cell types in a medium in one or more wells of the multiwell culture plate of aspect 3; fitting said wedge under said multiwell culture plate, optionally vibrating said plate; removing said wedge when all cells have collected at said vertex; and imaging said cells through said flat base.

21. The method of aspect 19 or 20, wherein said vibrating step is performed.

22. A multiwell culture plate, comprising: a rectangular plate having a long side and a short side; said plate having a plurality of wells; and each of said plurality of wells having a V-shaped cross section when viewed from a top view, said V-shaped cross section having a vertex; and each of said wells having a flat base.

23. A multiwell culture plate, comprising: a rectangular plate having a long side and a short side; said plate having a plurality of wells; and each of said plurality of wells having a triangular cross section when viewed from a top view, said triangular cross section having a vertex; and each of said wells having a transparent flat base.

24. A method of imaging a cell culture, comprising: incubating one or more cell types in a medium in one or more wells of a multiwell culture plate wherein each well has a transparent flat base; tilting said multiwell culture plate; vibrating said multiwell culture plate; collecting all cells at a lowest location of said one or more wells of said tilted multiwell culture plate; ceasing said tilting and said vibrating; and, imaging said cells through said transparent flat base.

25. The method of aspect 24, where said one or more wells have a triangular or a square or a V-shaped cross section having at least one vertex, and wherein said tilting allows cells to collect at said vertex.

26. The method of aspect 25, wherein said vertex has a rounded corner.

27. A multiwell culture plate, comprising: a rectangular plate having a long side and a short side; said plate having a plurality of wells; and each of said plurality of wells having a V-shaped cross section at a base of said wells, said V-shaped cross section having a vertex and a first leg and a second leg; wherein said first legs of each well in a single row are connected near a top surface of said plate, thus forming a channel connecting all wells in said row; and each base being a flat transparent base.

28. The multiwell culture plate of aspect 27, wherein each said channel connects to a same end channel allowing collection of all cells in all rows of said multiwell culture plate.

29. A method of imaging a cell culture, comprising: incubating one or more cell types in a medium in one or more wells of the multiwell culture plate of aspect 28; tilting said multiwell culture plate; vibrating said multiwell culture plate; collecting all cells at said vertex of each well in said tilted multiwell culture plate; ceasing said tilting and said vibrating; and, imaging said cells through said transparent flat base.

30. The method of aspect 29, wherein said tilting to an opposite end of the said vertex, allows cells from a row of wells to be collect together.

The above descriptions are illustrative only and not intended to unduly limit the invention as defined by the appended claims.

The following are incorporated by reference herein in its entirety for all purposes:
ANSI SLAS 1-2004 (R2012): Footprint Dimensions
ANSI SLAS 2-2004 (R2012): Height Dimensions
ANSI SLAS 3-2004 (R2012): Bottom Outside Flange Dimensions
ANSI SLAS 4-2004 (R2012): Well Positions
ANSI SLAS 4-2012: Well Bottom Elevation
WO2013019212, US20140220672, and 61/372,164, filed Aug. 10, 2010
US20120171744 U.S. Pat. No. 8,883,471 US20150104844 and 61/245,846, which was filed on Sep. 25, 2009, Materials for magnetizing cells and magnetic manipulation
US20150091233 PHONE CAMERA AND SAMPLE STAND
US20110286975 U.S. Pat. No. 8,815,231, US20140322784 and 61/099,966, filed Sep. 25, 2008, Systems and methods for magnetic guidance and patterning of materials
U.S. Pat. No. 5,225,164 Microplate laboratory tray with rectilinear wells
U.S. Pat. No. 5,002,582 Preparation of polymeric surfaces via covalently attaching polymers
U.S. Pat. No. 5,457,527 Microplate forming wells with transparent bottom walls for assays using light measurements
U.S. Pat. No. 6,503,456 Microplate with transparent base
U.S. Pat. No. 6,340,589 Thin-well microplate and methods of making same
US20050170498 Multiwell plate and method for making multiwell plate using a low cytotoxicity photocurable adhesive
U.S. Pat. No. 8,512,652 Multiwell microplate with transparent bottom having a thickness less than 200 micrometers
U.S. Pat. No. 7,599,055 Swept wavelength imaging optical interrogation system and method for using same
U.S. Pat. No. 7,265,829 Reflective optic system for imaging microplate readers
US20110286102 Optical Adaptor
U.S. Pat. No. 6,130,745 Optical autofocus for use with microtiter plates
U.S. Pat. No. 8,636,965 Microtitration plate
U.S. Pat. No. 9,168,532 Microwell plate
Castro-Chavez, F., et al., Effect of lyso-phosphatidylcholine and Schnurri-3 on osteogenic transdifferentiation of vascular smooth muscle cells to calcifying vascular cells in 3D culture. *Biochim. Biophys. Acta* 1830, 3828-34 (2013).

Desai P. K., et al. Assembly of Hepatocyte Spheroids Using Magnetic 3D Cell Culture for CYP450 Inhibition/Induction. Int J Mol Sci, In Press, 2017.

Ferreira J. N., et al. Three-dimensional Bioprinting Nanotechnologies Towards Clinical Application of Stem Cells and their Secretome in Salivary Gland Regeneration. Stem Cells Int, 7564689 (2016).

Haisler W. L., et al. Three-dimensional cell culturing by magnetic levitation. Nat Protoc, 8: 1940-9 (2013).

Souza G. R., et al. Magnetically bioprinted human myometrial 3D cell rings as a model for uterine contractility. Int J Mol Sci, In Press (2017).

Souza, G. R., et al. Three-dimensional tissue culture based on magnetic cell levitation. *Nat. Nanotechnol.* 5, 291-6 (2010).

Timm, D. M., et al. A high-throughput three-dimensional cell migration assay for toxicity screening with mobile device-based macroscopic image analysis. Sci. Rep. 3, 3000 (2013).

Tseng H., et al. A high-throughput in vitro ring assay for vasoactivity using magnetic 3D. Sci Rep, 6:30640, 2016.

Tseng H., et al. A spheroid toxicity assay using magnetic 3D bioprinting and real-time mobile device-based imaging. Sci Rep, 5:13987, 2015.

Tseng, H. et al. Assembly of a three-dimensional multitype bronchiole coculture model using magnetic levitation. *Tissue Eng. Part C. Methods* 19, 665-75 (2013).

Tseng, H. et al. A three-dimensional co-culture model of the aortic valve using magnetic levitation. *Acta Biomater.* 10, 173-82 (2014).

The invention claimed is:

1. A multiwell culture plate system, comprising:
 (a) a multiwell culture plate, comprising:
  i) a rectangular plate having a first and second long side and a first and second short side;
  ii) said plate having a plurality of wells; and,
  iii) each of said plurality of wells having a non-circular cross section having at least one vertex when viewed from a top view; and
  iv) each of said wells having a flat transparent base lacking any obstruction, such that the entirety of the well contents can be imaged from underneath the base;
 (b) a rectangular cap having a lip around an outer circumference thereof and being shaped to fit over or under said rectangular plate; and
 (c) a rectangular wedge for tilting said plate, wherein the rectangular wedge has a flat top surface and fits and is slippable under said rectangular plate thus lifting said second long side or said second short side by 15-45°.

2. The multiwell culture plate system of claim 1, wherein the non-circular cross section is a V-shaped cross section when viewed from a top view.

3. The multiwell culture plate system of claim 1, wherein the non-circular cross section is a triangular cross section when viewed from a top view.

4. The multiwell culture plate system of claim 1, said vertex oriented to said first long side or said first short side.

5. The multiwell culture plate system of claim 1, said vertex having a rounded corner.

6. The multiwell culture plate system of claim 1, said rectangular cap having a plurality of magnets affixed thereto, thus holding said magnet over or under each said well when said cap is in place over or under said multiwell culture plate.

7. The multiwell culture plate system of claim 1, said rectangular cap having a plurality of magnets affixed thereto, thus holding said magnet over each said well when said cap is in place over or under said multiwell culture plate, each adjacent magnet being in an opposite polarity.

8. The multiwell culture plate system of claim 7, wherein each said magnet sits over each said vertex.

9. The multiwell culture plate system of claim 7, wherein each said magnet sits over a center of each well.

10. The multiwell culture plate system of claim 1, having 6, 24, 96, 384, 1536, 3072 or 6144 wells.

11. A method of imaging a cell culture, comprising:
 a) incubating one or more cell types in a medium in one or more wells of the multiwell culture plate of a multiwell culture plate system according to claim 1;
 b) tilting said multiwell culture plate so that cells collect at said vertex;
 c) optionally vibrating said plate;
 d) removing said tilt when all cells have collected at said vertex; and
 e) imaging said cells through said flat transparent base.

12. A method of imaging a cell culture, comprising:
 a) incubating one or more cell types in a medium in one or more wells of the multiwell culture plate of a multiwell culture plate system according to claim 1;
 b) fitting the rectangular wedge under said multiwell culture plate,
 c) optionally vibrating said plate;
 d) removing said wedge when all cells have collected at said vertex; and
 e) imaging said cells through said flat transparent base.

13. A method of imaging a cell culture, comprising:
 a) incubating one or more cell types in a medium in one or more wells of a multiwell culture plate, wherein each well has a flat transparent base;
 b) tilting said multiwell culture plate;
 c) vibrating said multiwell culture plate;
 d) collecting all cells at a lowest location of said one or more wells of said tilted multiwell culture plate;
 e) ceasing said tilting and said vibrating; and,
 f) imaging said cells through said transparent flat base;
 wherein said one or more wells have a V-shaped cross section having at least one vertex,
 wherein said tilting allows cells to collect at said vertex, and
 wherein the multiwell culture plate is the multiwell culture plate of a multiwell culture plate system, the multiwell culture plate system comprising:
 a. the multiwell culture plate that comprises
  i. a rectangular plate having a first and second long side and a first and second short side;
  ii. said plate having a plurality of wells;
  iii. each of said plurality of wells having a V-shaped cross section having at least one vertex when viewed from a top view; and
  iv. each of said wells having a flat transparent base lacking any obstruction, such that the entirety of the well contents can be imaged from underneath the base;

b. a rectangular cap having a lip around an outer circumference thereof and being shaped to fit over or under said rectangular plate; and
c. a rectangular wedge for tiling said plate, wherein the rectangular wedge has a flat top surface and fits and is slippable under said rectangular plate thus lifting said second long side or said second short side by 15-45°.

* * * * *